(12) United States Patent
Lau

(10) Patent No.: US 11,911,404 B2
(45) Date of Patent: Feb. 27, 2024

(54) FUCOSYLATION AND IMMUNE SURVEILLANCE IN MELANOMA

(71) Applicant: H. LEE MOFFITT CANCER CENTER AND RESEARCH INSTITUTE, INC., Tampa, FL (US)

(72) Inventor: Eric Lau, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 623 days.

(21) Appl. No.: 16/755,703

(22) PCT Filed: Oct. 15, 2018

(86) PCT No.: PCT/US2018/055810
§ 371 (c)(1),
(2) Date: Apr. 13, 2020

(87) PCT Pub. No.: WO2019/075449
PCT Pub. Date: Apr. 18, 2019

(65) Prior Publication Data
US 2020/0330494 A1    Oct. 22, 2020

Related U.S. Application Data

(60) Provisional application No. 62/686,675, filed on Jun. 19, 2018, provisional application No. 62/572,261, filed on Oct. 13, 2017.

(51) Int. Cl.
| | | |
|---|---|---|
| *A61K 31/70* | (2006.01) | |
| *A61K 31/7004* | (2006.01) | |
| *A61K 9/00* | (2006.01) | |
| *A61K 39/395* | (2006.01) | |
| *C12Q 1/686* | (2018.01) | |
| *G01N 33/574* | (2006.01) | |
| *G01N 33/58* | (2006.01) | |

(52) U.S. Cl.
CPC ........ *A61K 31/7004* (2013.01); *A61K 9/0053* (2013.01); *A61K 39/3955* (2013.01); *C12Q 1/686* (2013.01); *G01N 33/5743* (2013.01); *G01N 33/58* (2013.01); *G01N 2333/70539* (2013.01); *G01N 2458/00* (2013.01)

(58) Field of Classification Search
CPC .............. A61K 31/7004; A61K 9/0053; A61K 39/3955; C12Q 1/686; C12Q 1/6804; G01N 33/5743; G01N 33/58; G01N 2333/70539; G01N 2458/00; G01N 33/57426; G01N 2333/4724; G01N 2400/02; G01N 2440/38; G01N 2458/10; G01N 2800/52
See application file for complete search history.

(56) References Cited

FOREIGN PATENT DOCUMENTS

| WO | 2017096274 A1 | 6/2017 | |
|---|---|---|---|
| WO | WO 2017/096274 | * 6/2017 | ......... A61K 31/2074 |

OTHER PUBLICATIONS

International Search Report and Written Opinion in PCT/US2018/055810. dated Mar. 25, 2019. 10 pages.
Lau et al. The transcription factor ATF2 promotes melanoma metastasis by suppressing protein fucosylation. Sci. Signa, Dec. 8, 2015, vol. 8, No. 406, pp. ra124 1-12.
Gabrilovich. Myeloid-Derived Suppressor Cells. Cancer Immunol Res, Jan. 2015, vol. 5, No. 1, pp. 3-8.

\* cited by examiner

*Primary Examiner* — Nelson B Moseley, II
(74) *Attorney, Agent, or Firm* — Meunier Carlin & Curfman LLC

(57) ABSTRACT

Disclosed are methods for treating a cancer and/or enhancing immune responses to infiltration of tumors comprising administering to a subject a fucose. Also disclosed herein are methods of detecting the presence of a sugar-modified protein (i.e., a glycosylated protein).

9 Claims, 22 Drawing Sheets

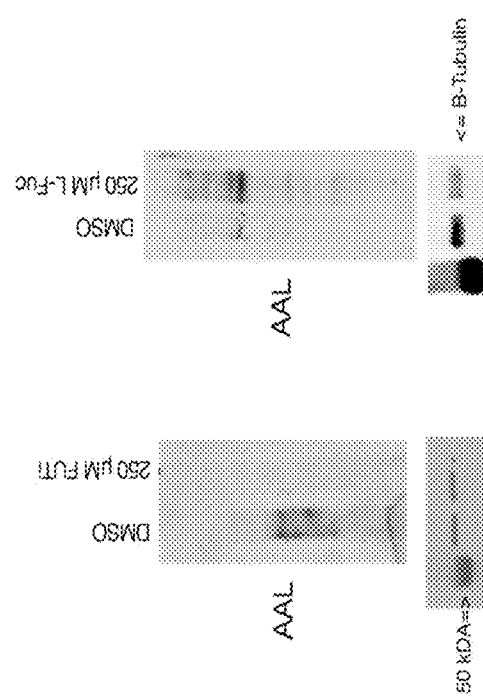
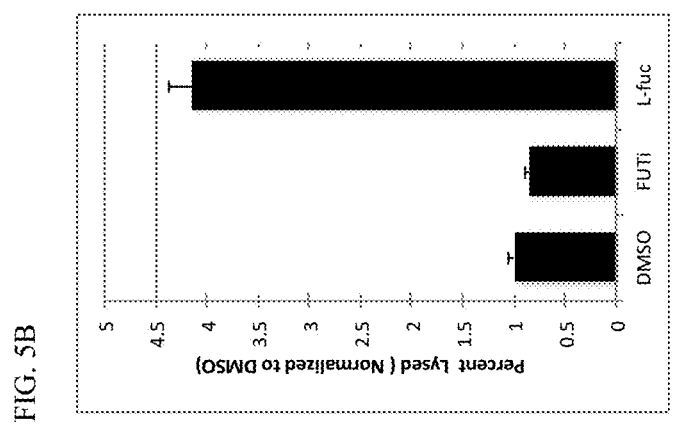
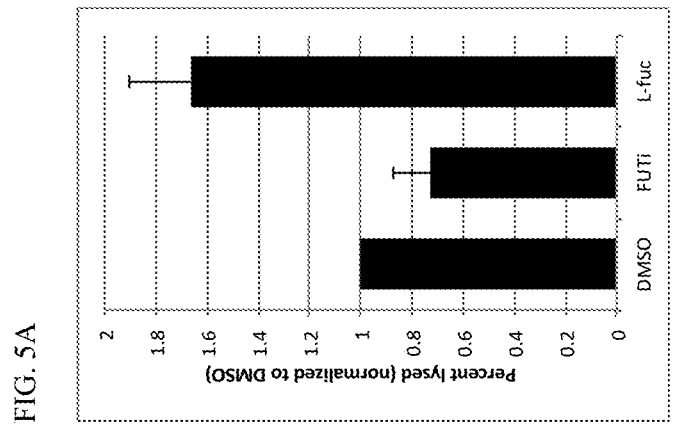
FIG. 5A  FIG. 5B  FIG. 5C  FIG. 5D

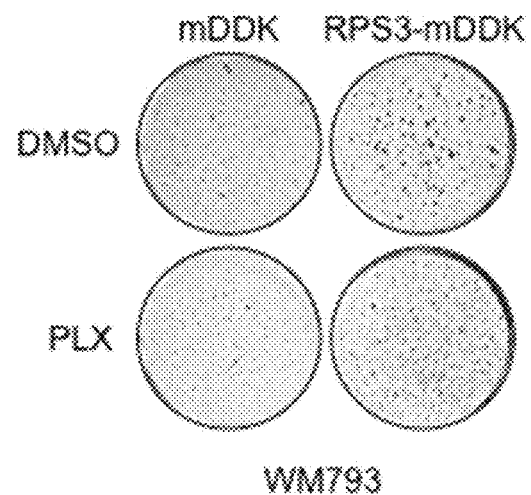
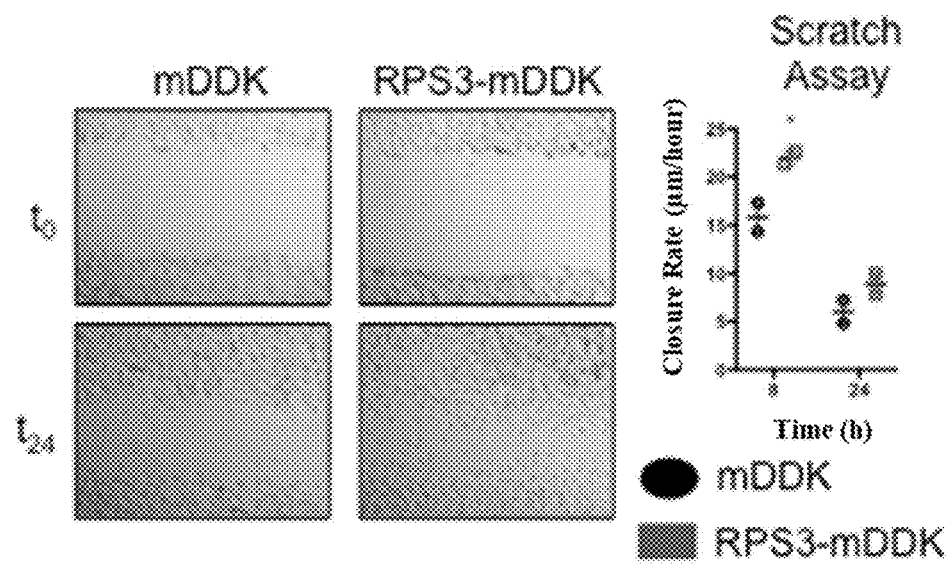
FIG. 11D

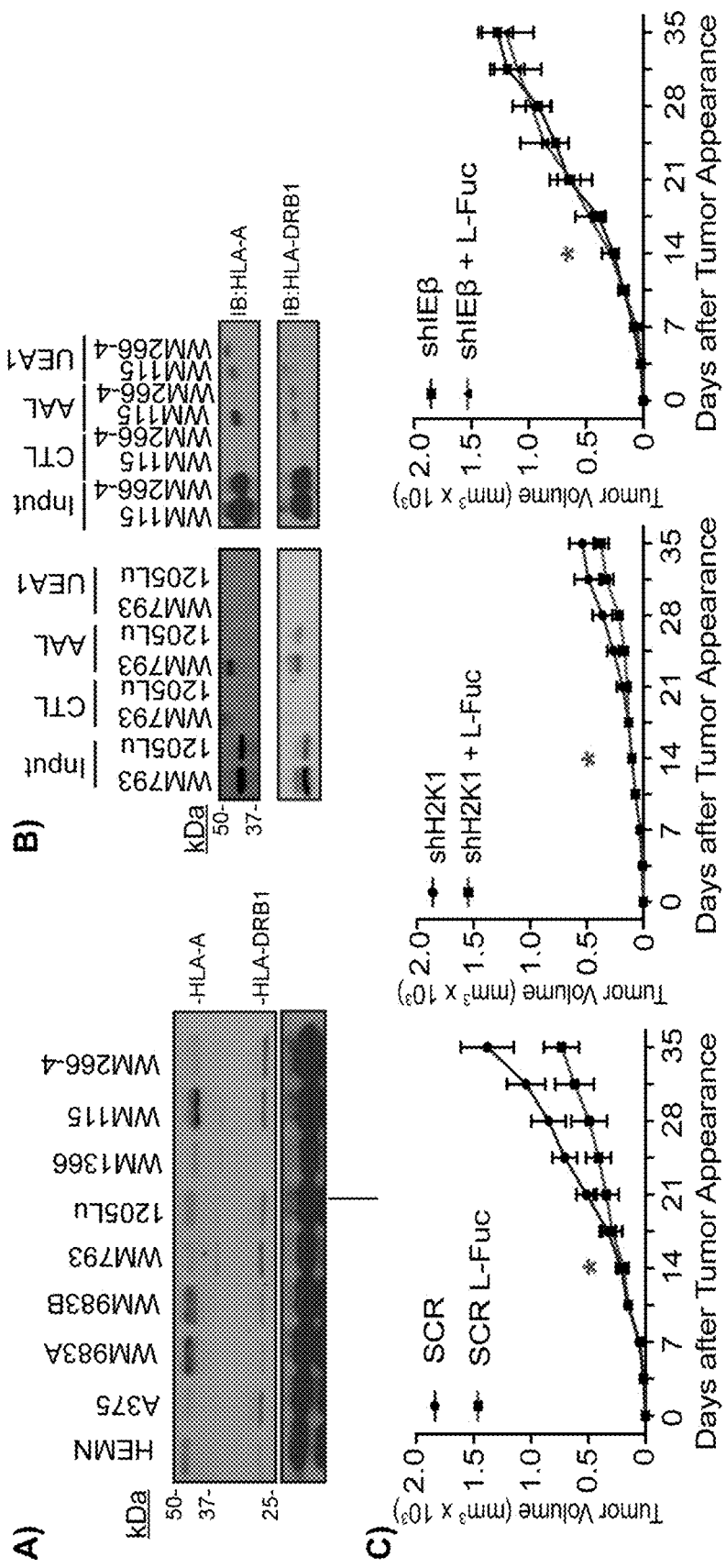
FIG. 15A, FIG. 15B, and FIG. 15C

FUCOSYLATION AND IMMUNE SURVEILLANCE IN MELANOMA

CROSS REFERENCE TO RELATED APPLICATIONS

This application is a United States National Phase Patent Application filed under 35 U.S.C. § 371 of International Patent Application Number PCT/US2018/055810, filed on Oct. 15, 2018, which claims the benefit of U.S. Provisional Application No. 62/572,261, filed Oct. 13, 2017, and U.S. Provisional Application No. 62/686,675, filed Jun. 19, 2018, which are incorporated herein by reference in their entirety.

STATEMENT OF GOVERNMENT SUPPORT

This invention was made with Government support under Grant No. CA172705 awarded by the National Institutes of Health. The Government has certain rights in the invention.

I. BACKGROUND

Melanoma is one of the most lethal skin cancers worldwide, characterized by a striking ability to metastasize and develop therapeutic resistance. The immune system plays a crucial role in recognizing and suppressing cancers in the body. Unfortunately, melanomas can interact with and inactivate immune cells. Currently, among the most effective anti-melanoma therapies is immunotherapies. These include antibody-based immunotherapies, such Nivolumab or Ipilumumab, which block these inhibitory interactions, "reactivating" the tumor-suppressing activities of immune cells, as well as adoptive cell ("TIL") therapy which involves the ex vivo expansion of tumor-infiltrating lymphocytes. However, despite recent successes of such immunotherapies, responsiveness (and durations of responses) is limited to subsets of patients. What are needed are new immunotherapies that can overcome the limitations of existing therapeutic protocols.

II. SUMMARY

Disclosed are methods related to enhancing immune responses and treating cancers with the administration of fucose.

In one aspect, disclosed herein are methods of increasing the number of tumor infiltrating lymphocytes (such as, for example NK cells, dendritic cells, and T cells) at least 10-fold in a subject with a tumor comprising administering fucose (L-fucose, D-fucose, fucose-1-phosphate, or GDP-L-fucose) to the subject.

Also disclosed herein are methods of increasing the number of tumor infiltrating lymphocytes, wherein the fucose is administered orally.

Also disclosed herein are methods of any preceding aspect, wherein the method further results in at least a 20% reduction in myeloid-derived suppressor cells.

In one aspect, disclosed herein are methods of treating a cancer in a subject comprising administering to the subject fucose (L-fucose, D-fucose, fucose-1-phosphate, or GDP-L-fucose) and an anti-tumor agent (such as, for example, a chemotherapeutic agent, antibody, or checkpoint inhibitor (such as, for example, PD-1 inhibitors lambrolizumab, OPDIVO® (Nivolumab), KEYTRUDA® (pembrolizumab), and pidilizumab; PD-L1 inhibitors BMS-936559, TECENTRIQ® (Atezolizumab), IMFINZI® (Durvalumab), and BAVENCIO® (Avelumab); and CTLA-4 inhibitors YERVOY (ipilimumab)).

In one aspect, disclosed herein are methods of detecting a sugar modified protein (such as, for example HLA-DRB1) comprising a) contacting the protein of interest with a first antibody that specifically binds to the protein of interest and a lectin (such as, for example, Ulex europaeus agglutinin 1 (UEA1) or Aleuria aurantia lectin (AAL)) that recognizes the sugar modification of interest; b) contacting the lectin with a second antibody that specifically binds to the lectin; c) contacting the first antibody that bound the protein of interest with a third antibody that specifically binds the first antibody and contacting the second antibody with a fourth antibody that recognizes the second antibody; wherein the third and fourth antibodies are conjugated to complementary oligonucleotides; d) annealing the oligonucleotides, and e) amplifying the annealed oligonucleotides by a polymerase chain reaction (PCR).

In one aspect, disclosed herein are methods of detecting the presence of a sugar-modified protein, wherein the lectin comprises a detectable label (such as, for example, biotin).

In one aspect, disclosed herein are methods of detecting the presence of a sugar-modified protein of any preceding aspect, wherein the second antibody binds to the label on the lectin.

Also disclosed herein are methods of detecting the presence of a sugar-modified protein of any preceding aspect, wherein the first antibody comprises a detectable label.

In one aspect, disclosed herein are methods of detecting the presence of a sugar-modified protein of any preceding aspect, wherein the third and fourth antibody comprise the same specificity.

Also disclosed herein are methods of detecting the presence of a sugar-modified protein of any preceding aspect, wherein the PCR reaction is a rolling circle PCR amplification reaction.

In one aspect, disclosed herein are methods of detecting the presence of checkpoint inhibitors in a cancer comprising detecting a sugar modified protein (such as, for example HLA-DRB1) comprising obtaining a cancerous tissue sample from a subject, subjecting the tissue sample to lectin-mediated proximity ligation (L-PLA) for fucosylated HLA-DRB1, lectin (such as, for example, Aleuria aurantia lectin (AAL)) pulldown, or flow cytometry with an anti-lectin or antibody specific for the sugar modified protein; wherein the presence of a sugar modified protein on the cancer cell indicates the presence of a checkpoint inhibitor on the surface of a cancer cell. In one aspect, the L-PLA can be for microscopy or flow cytometry.

III. BRIEF DESCRIPTION OF THE DRAWINGS

The accompanying drawings, which are incorporated in and constitute a part of this specification, illustrate several embodiments and together with the description illustrate the disclosed compositions and methods.

FIGS. 1A, 1B, and 1C show that fucosylation decreases through melanoma progression. FIG. 1A shows that immunostaining for fucosylated proteins of a melanoma tumor. FIG. 1B shows the measuring of UEA1 in HMB45/S100-positive melanoma cells. FIG. 1C shows the correlation of the level of UEA1 plotted against survival probability.

FIGS. 2A and 2B show that Dietary and Genetic modulation of the fucose pathway leads to tumor suppression as shown by supplementation of fucose (2A) and overexpression of mouse FUK (2B).

FIGS. 2C and 2D show that Dietary fucose supplementation triggers increased leukocyte and NK cell infiltration of melanoma tumors. FIG. 2C shows immunofluorescent staining of a tissue sample with CD45 (general leukocyte marker, red) and DAPI to show immune cell infiltration. FIG. 2D shows the effect of fucosylation on NK cell as measured by DX5 (NK cell marker, red) and DAPI.

FIGS. 3A and 3B show that dietary fucose increases immune infiltration of tumors, with a decrease in MDSCs and an increase in T cells. FIGS. 3A and 3B show the change in tumor volume following dietary fucose supplementation. FIGS. 3C and 3D show the change in (3C) total leukocytes and (3D) for T cells (CD3), CD4+ T cells (CD25), Dendritic cells (CD11c), NK cells (DX5), macrophage (F4/80), and myeloid derived suppressor cells (GR1) following dietary fucose supplementation.

FIGS. 4A, 4B, 4C, and 4D show that L-fucose triggers CD4+ T cell-dependent suppression of melanoma. FIG. 4A shows SW1 mouse melanoma tumor growth curves of mice fed with control (blue) or 100 mM L-fucose-supplemented (red) water over 45 days. FIG. 4B shows numbers of intratumoral CD4+ T (left) or CD8+ T (right) cells per g of tumor in control vs. L-fucose water-fed mice. FIG. 4C shows SW1 tumor growth curves in CD4+ T (left) or CD8+ T (right) cell-depleted mice fed with control (blue) or L-L-fucose (red) water over 45 days. FIG. 4D shows numbers of intratumoral CD8+ T (medium grey), NK (light grey) and dendritic (DC; black) cells per g of tumor in control (PBS) vs. CD4+ T-cell-depleted (−CD4) mice fed with control vs. L-fucose (+F) water.

FIGS. 5A, 5B, 5C, and 5D show that Melanoma fucosylation stimulated NK cell killing. FIG. 5 shows 1205LU cells pre-treated with DMSO (control), 250 μM fucosyltransferase inhibitor (FUTi), or 250 μM L-fucose that were co-cultured with immortalized (5A) or primary (5B) human NK cells. After 8 h, LDH levels released in the media were measured. *=p 0.02; •=p<0.001. FIGS. 5C and 5D show Immunoblot analysis using AAL lectin (another fucose-binding lectin) was performed to confirm the effects of FUTi (C) or L-fucose (D) on 1205Lu cells (96 h treatment). (•: p-value≥0.02)(*: p-value≥0.002).

FIGS. 6A, 6B, and 6C show that HLA-A and HLA-DRB1 are fucosylated in melanoma cell lines. The previous fucosylated protein mass spectrometric analyses identified HLA-A and HLA-DRB1 as fucosylated immunomodulatory proteins in melanoma cells. FIG. 6A shows immunoblot analysis for HLA-A, HLA-DRB1, and b-tubulin expression was performed on a panel of melanocyte and melanoma cell lines. FIG. 6B shows lectin-mediated proximity ligation assay performed on WM793 cells for fucosylated HLA-A (left) and HLA-DRB1 (right) (red), phalloidin (green), and DAPI (blue). FIG. 6C shows that UEA1 and AAL lectin pulldown was performed in WM793, 1205Lu, WM115, and WM266-4 cell lines, followed by immunoblot analysis for HLA-A and HLA-DRB1.

FIG. 7 shows Inhibiting fucosylation increases surface presentation of HLA-A and β2-microglobulin, but not HLA-DRB1. WM793 cells treated with DMSO (control, black) or 250 μM FUTi (grey) for 72 h stained with PKH26 (plasma membrane stain) and HLA-A, β2-microglobulin (B2M), or HLA-DRB1 antibodies. Stained cells were subjected to flow cytometric analyses and quantitation of protein signal/PKH26 signal to quantitate protein per relatice surface area.

FIGS. 11A, 11B, 11C, and 11D shows that RPS3 is increased in melanoma cells, shows a shift toward nuclear localization throughout progression, and confers an advanced phenotype.

Figure 12:
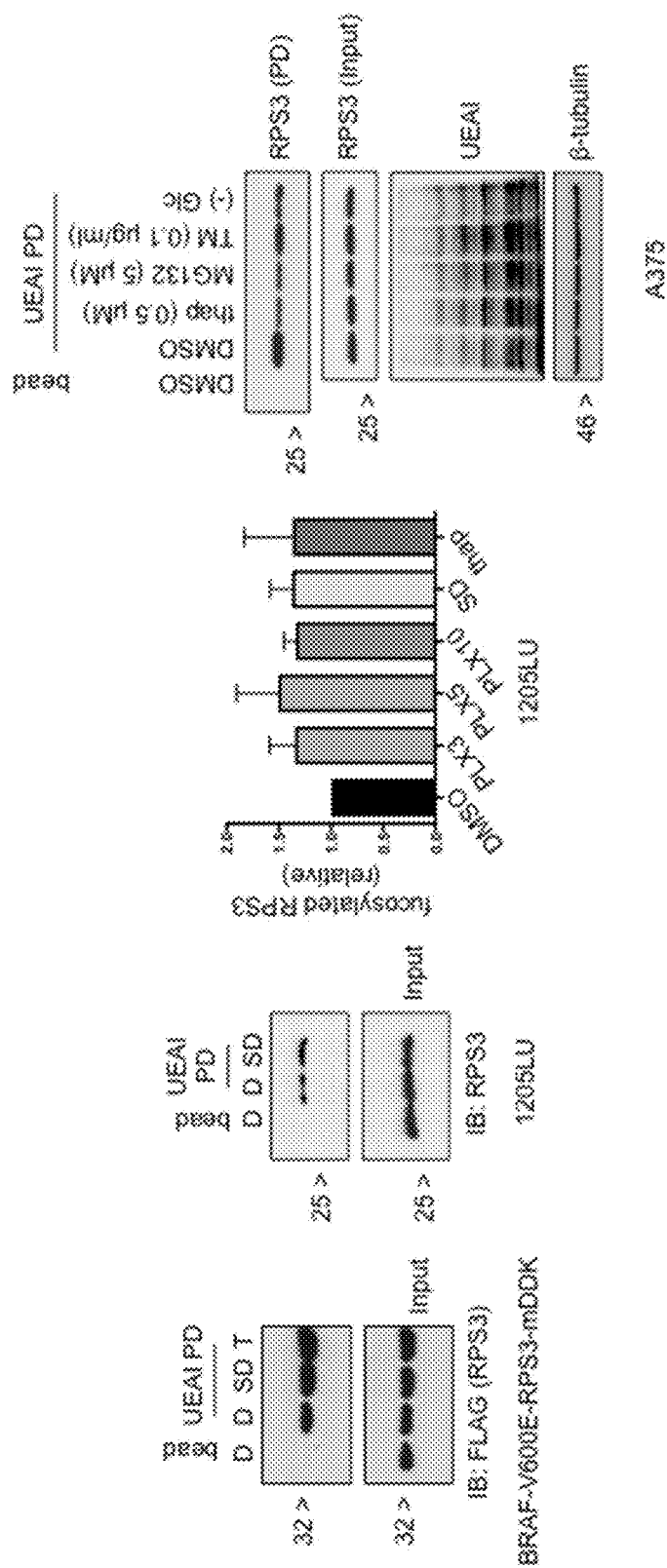

FIG. 12 shows that RPS3 fucosylation level responds to cellular stressors.

Figures 13A, 13B:
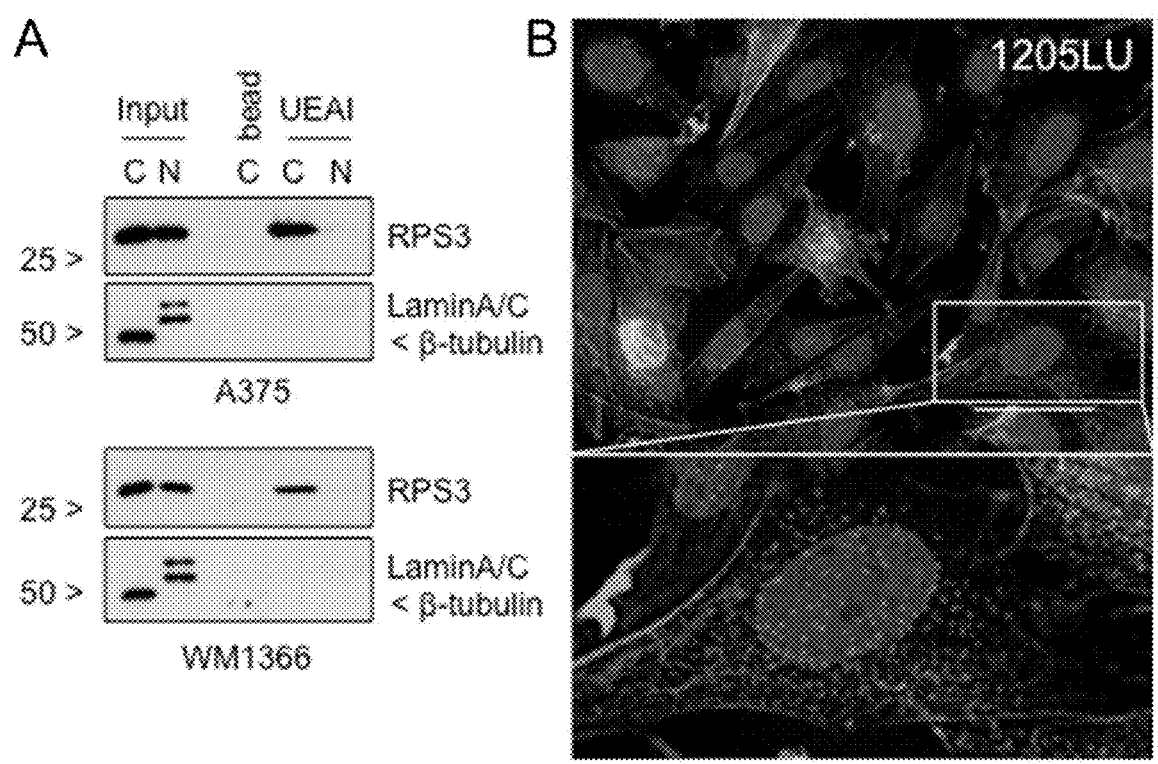

FIGS. 13A and 13B show that fucosylated RPS3 is found only in the cytoplasmic fraction (by lectin-mediated proximity ligation assay).

Figure 14:
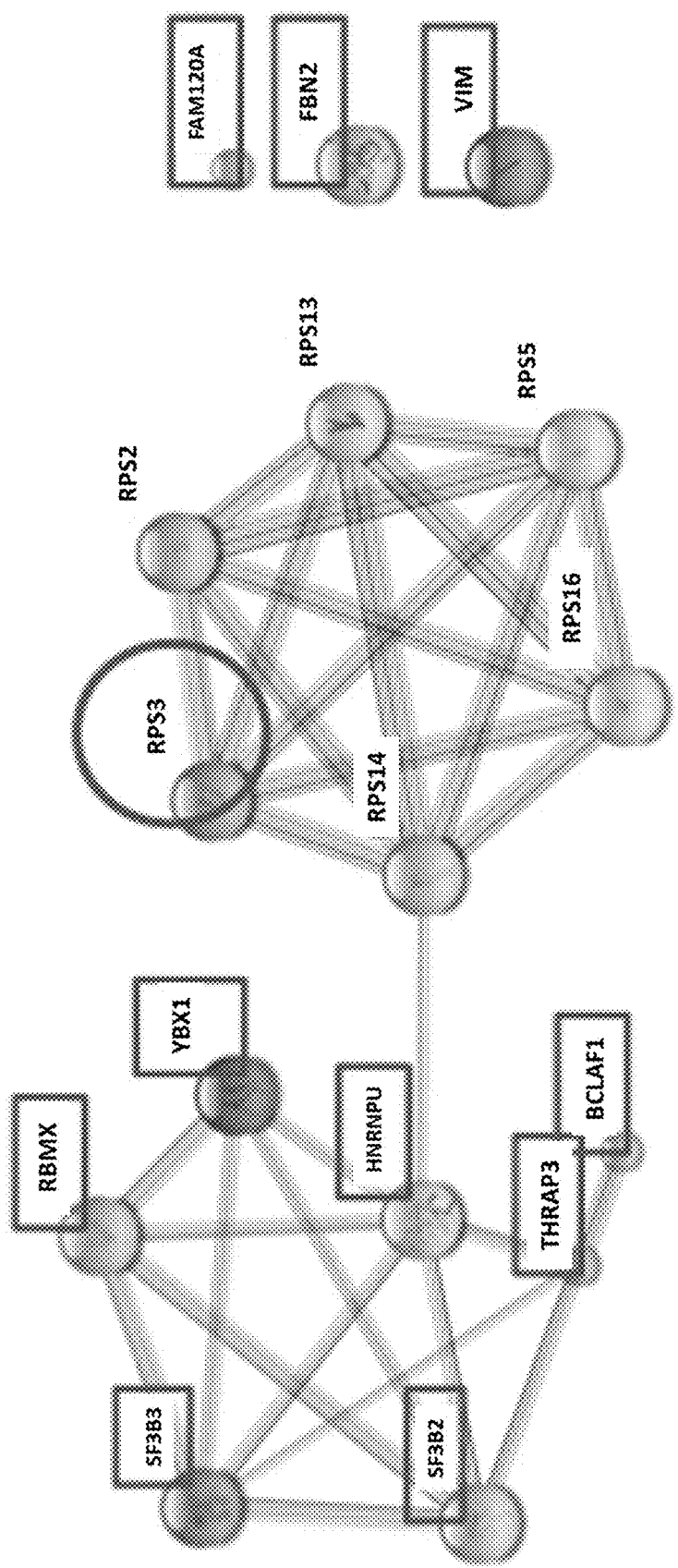

FIG. 14 shows that Fucosylated RPS3 binds to splicing factors.

FIGS. 15A, 15B, and 15C show that melanoma HLA-DRB1 is fucosylated and required for L-fucose-triggered melanoma suppression. FIG. 15A shows that human primary melanocytes (HEMN) or indicated melanoma cell lines immunoblotted (IB) for HLA-A, HLA-DRB1, and β-tubulin FIG. 15B shows that L-fucose-binding lectin (AAL & UEA1) pulldown of WM793 and 1205Lu or WM115 and WM266-4 patient-matched primary and metastatic cell line_pairs, IB for HLA-A and HLA-DRB1. FIG. 15C shows growth curves of control (SCR; left), H2K1 (shH2K1; center)- or Iβ (shIEβ)-knocked down tumors in mice fed±100 mM L-fuc water. N=7 mice/condition. •:p<0.01. Differences in ±L-fuc curves for shH2K1/shIE□ are not significant. (*initiate L-fucose).

Figures 16A, 16B:
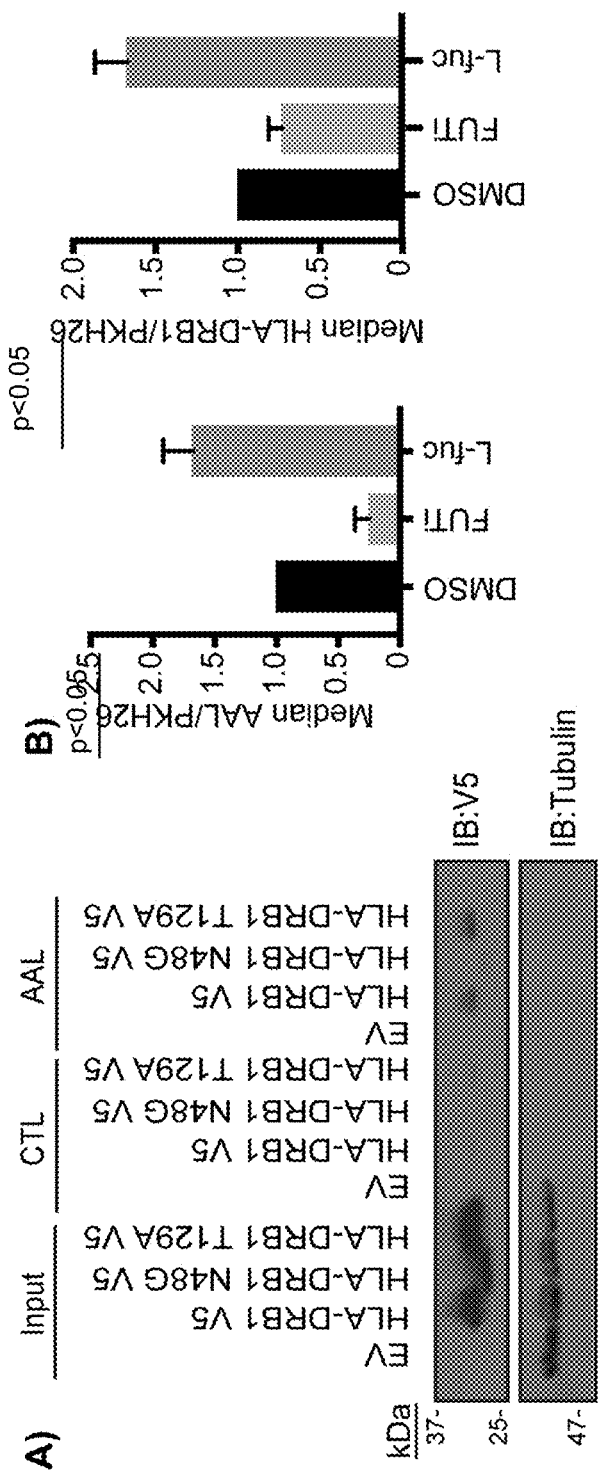

FIGS. 16A and 16B show HLA-DRB1 is fucosylated on N48, and fucosylation promotes its cell surface presentation. FIG. 16A shows AAL lectin pulldown of WM793 cells transduced to express V5-tagged wild type HLA-DRB1, N48G or T129A fucomutants of HLA-DRB1 followed by IB for V5 or β-tubulin. FIG. 16B shows flow cytometry quantitating cell surface fucosylation (AAL lectin binding, left) or HLA-DRB1 (right) of WM793 cells treated with DMSO, FUTi, or L-fuc. AAL or HLA-DRB1 signals were normalized to PKH26 (total membrane stain).

Figures 17A, 17B:
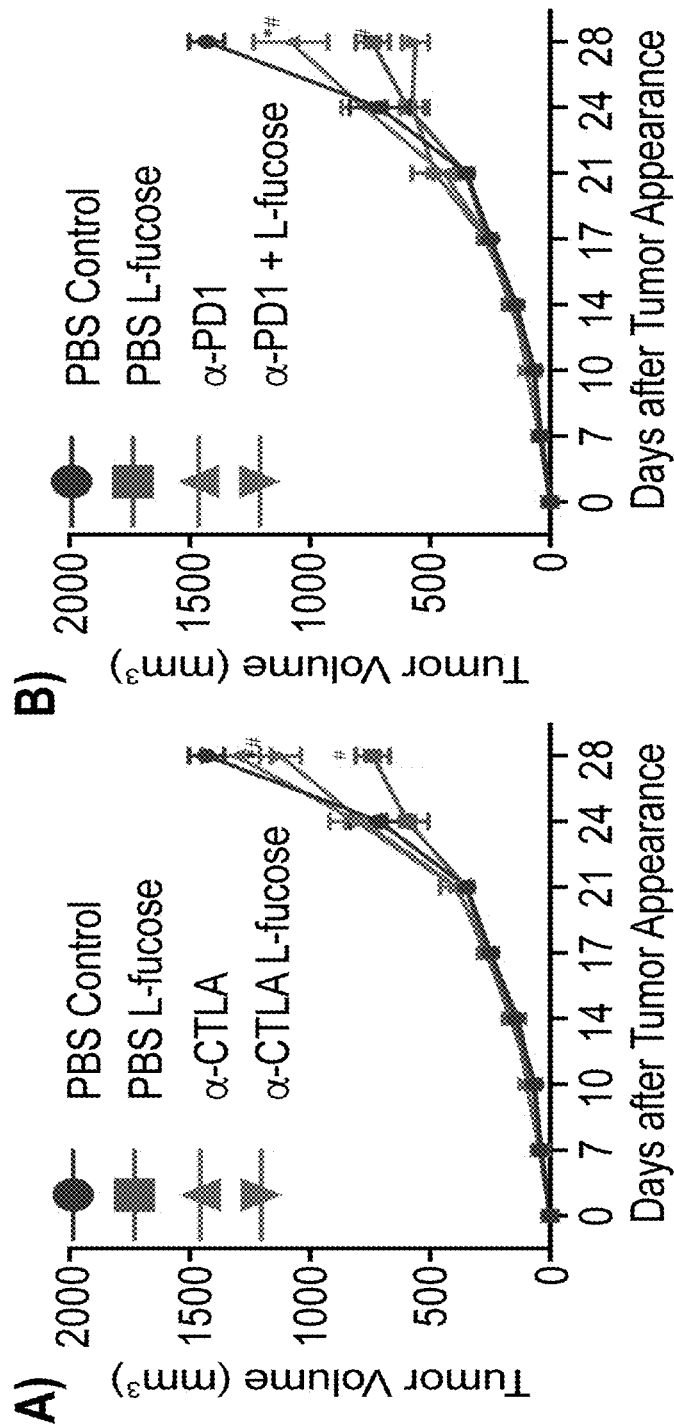
Figures 18A, 18B:
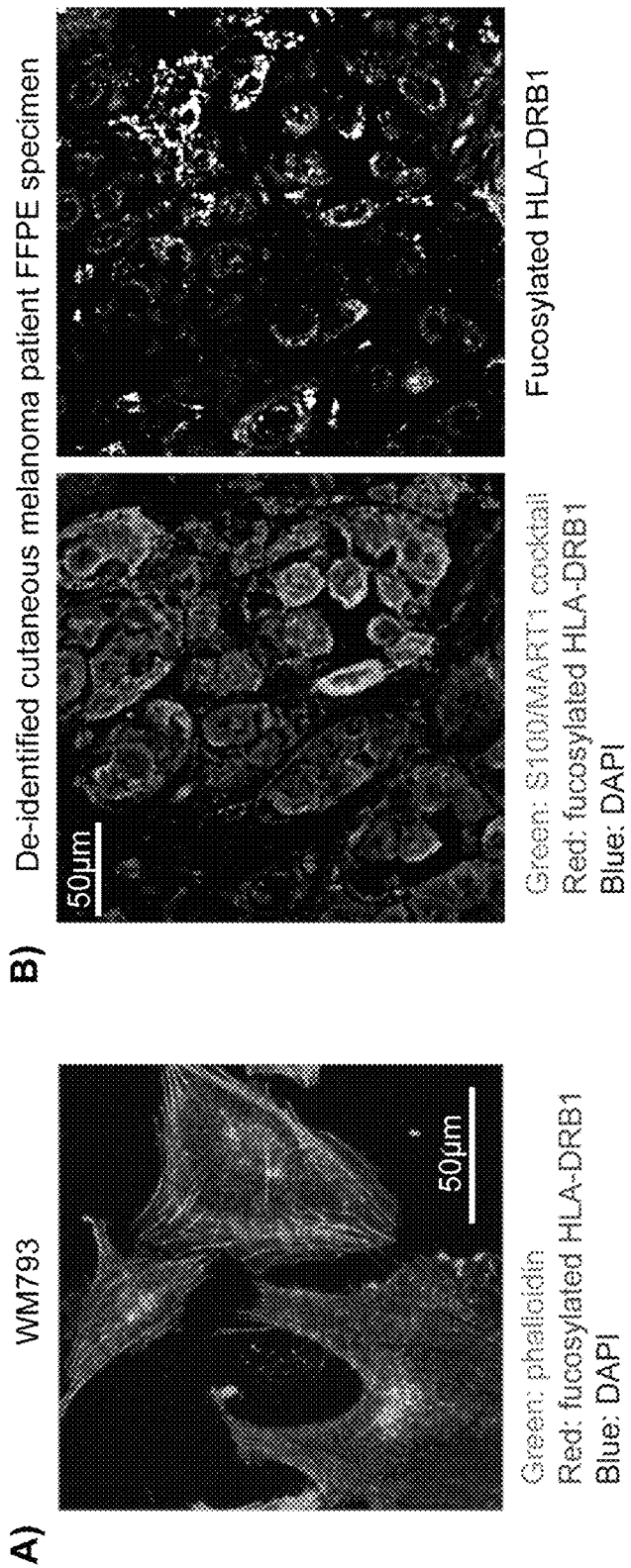

FIGS. 17A and 17B show Oral L-fucose is more tumor suppressive than α-CTLA4 or α-PD1 alone, beginnings of improved effects. SW1 tumor growth curves in mice fed±100 mM L-fucose treated with either control (PBS) or α-CTLA1 (17A) or α-PD1 (17B). Combinations are color-coded as indicated. N=8 mice per condition. L-fucose was administered in the water starting on day 14 (refreshed twice weekly); α-CTLA4 or α-PD1 was administered (20 mg/kg each) twice weekly starting day 14. Compared with PBS control: #: p<0.001; *: p<0.05:

FIGS. 18A and 18B show Lectin-mediated proximity ligation (L-PLA) visualizes fucosylated HLA-DRB1. Image of coverslip-grown WM793 cells (18A) or human melanoma tumor section (18B) subjected to L-PLA for fucosylated HLA-DRB1, color-coded as follows: •Green: phalloidin (cytoskeleton) (18A) or S100/MART1 (melanoma marker) cocktail (18B) •Red: fucosylated HLA-DRB1 (AAL+HLA-DRB1 L-PLA). •Blue: DAPI

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Fucosylation, the post-translational modification of proteins with the dietary sugar L-fucose, is a mechanism that is well established for its importance in immune cell biology and organ developmental processes but that is poorly understood in terms of its roles in cancer. Fucose is transported extracellularly through the plasma membrane, where it is first phosphorylated by fucokinase (FUK). Then it is conjugated with GDP, yielding GDP-Fucose, which is a usable form in the cell. GDP-Fucose is transported into the ER/Golgi through SLC35C1/2, where it can be conjugated to a serine/threonine via an oxygen, which is referred to as O'-linked fucosylation, or to an arginine via a nitrogen, which is referred to as N'-linked fucosylation. The fucosylated protein can then be either trafficked to the cytoplasm or the cell surface. Global fucosylation is reduced during progression in human melanomas (UEA1 fucose-binding lectin staining analysis of tumor microarray (TMA; n=~300 patients)) via an ATF2-mediated transcriptional repression of fucokinase (FUK). Importantly, increasing fucosylation by genetic manipulation of tumor cells or by dietary L-fucose supplementation significantly blocks tumor growth and metastasis by >50% in mouse models. The studies herein demonstrate that i) tumor fucosylation levels can be used to identify different stages of cancer, and ii), the manipulation of fucosylation represents a feasible anti-cancer approach.

In one aspect, disclosed are methods related to enhancing immune responses via the administration of fucose (for example as a composition comprising fucose including, but not limited to L-fucose, D-fucose, fucose-1-phosphate, or GDP-L-fucose). The disclosure herein shows that through the administration of fucose, NK cells, T cells (including CD4+ T cells and CD8+ T cells), dendritic cells, and macrophage increased in expression 10-50 fold. Accordingly, in one aspect, disclosed herein are methods of increasing the number of tumor infiltrating lymphocytes (such as, for example NK cells, dendritic cells, and T cells) at least 10, 11, 12, 13, 14, 15, 16, 17, 18, 19, 20, 21, 22, 23, 24, 25, 30, 35, 40, 45, or 50-fold (for example between about 10-fold and about 50-fold) in a subject with a tumor comprising administering fucose to the subject. It is understood that the methods of increasing the number of tumor infiltrating lymphocytes, wherein the fucose is administered orally. It is understood and herein contemplated that the increase in immune effector cells can coincide with a subsequent decrease in immune suppressor cells. Thus, in one aspect, disclosed herein are methods of any preceding aspect, wherein the method further results in at least a 20% reduction in myeloid-derived suppressor cells.

The fucose comprising compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The fucose (such as, for example, L-fucose, D-fucose, fucose-1-phosphate, or GDP-L-fucose) comprising compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the fucose comprising compositions into the nose and nasal passages through one or both of the nares and can comprise delivery by a spraying mechanism or droplet mechanism, or through aerosolization of the nucleic acid or vector. Administration of the fucose comprising compositions by inhalant can be through the nose or mouth via delivery by a spraying or droplet mechanism. Delivery can also be directly to any area of the respiratory system (e.g., lungs) via intubation. The exact amount of the fucose comprising compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the fucose comprising composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration.

Molecular and cellular mechanisms of receptor-mediated endocytosis has been reviewed (Brown and Greene, *DNA and Cell Biology* 10:6, 399-409 (1991)).

The fucose comprising compositions can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringers solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The fucose comprising compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Fucose comprising compositions for oral administration include powders or granules, suspensions or solutions in water or non-aqueous media, capsules, sachets, or tablets. Thickeners, flavorings, diluents, emulsifiers, dispersing aids or binders may be desirable.

Some of the fucose comprising compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering the fucose comprising compositions may be determined empirically, and making such determinations is within the skill in the art. The dosage ranges for the administration of the fucose comprising compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

As disclosed herein, the administration of fucose can expand TIL production. In the production of TILs, once a surgically resectable tumor has been obtained, the tumor is typically cut into small fragments and multiple fragments placed into wells of a culture plate where initial TIL expansion (referred to as "Pre-REP") occurs. The initially expanded TIL population is then subject for a second round of expansion (referred to as "REP") in tissue culture flasks. As disclosed herein, administration of the fucose or fucose comprising composition can occur at any time before, during, or after production of TILs including, but not limited to before, during, or after pre-REP or before, during, or after REP. In other words, administration of fucose can occur before pre-REP can occur at least 96, 84, 72, 60, 48, 36, 24, 18, 12, 8, 6, 5, 4, 3, 2, 1 hrs, 45, 30, 15, 10, or 5 minutes before the pre-REP expansion, concurrent with the commencement of pre-REP expansion, or at least 1, 2, 3, 4, 5, 10, 15, 30, 45 minutes, 1, 2, 3, 4, 5, 6, 7, 8, 9, 10, 11, 12, 18, 24, 36, 48, 60, 72, 84, or 96 hours after the commencement of the pre-REP expansion. Similarly, administration of fucose can occur before REP expansion can occur at least 96, 84, 72, 60, 48, 36, 24, 18, 12, 8, 6, 5, 4, 3, 2, 1 hrs, 45, 30, 15, 10, or 5 minutes before the REP expansion, concurrent with the commencement of pre-REP expansion, or at least 1, 2, 3, 4, 5, 10, 15, 30, 45 minutes, 1, 2, 3, 4, 5, 6, 7, 8, 9, 10, 11, 12, 18, 24, 36, 48, 60, 72, 84, or 96 hours after the commencement of the REP expansion. In one aspect, fucose can be administered to the subject in vivo following REP expansion of TILS and before, concurrently with, or after administration of TILs grown ex vivo are transferred to a subject in need thereof. Thus in one aspect, the expansion of TILS via fucosylation can occur in vivo. In one aspect, fucose can be administered at least 96, 84, 72, 60, 48, 36, 24, 18, 12, 8, 6, 5, 4, 3, 2, 1 hrs, 45, 30, 15, 10, or 5 minutes before the transfer of ex vivo expanded TILs, concurrent with the administration of TIls, or at least 1, 2, 3, 4, 5, 10, 15, 30, 45 minutes, 1, 2, 3, 4, 5, 6, 7, 8, 9, 10, 11, 12, 18, 24, 36, 48, 60, 72, 84, or 96 hours after the administration of TILs to the subject.

In one aspect, disclosed herein are methods of treating a cancer in a subject comprising administering to the subject fucose (such as for example, L-fucose, D-fucose, fucose-1-phosphate, or GDP-L-fucose) and anti-tumor agent (such as, for example, PD1/PDL1 blockade inhibitors and/or CTLA4/B7-1 or 2 inhibitors (such as, for example, PD-1 inhibitors lambrolizumab, OPDIVO® (Nivolumab), KEYTRUDA® (pembrolizumab), and pidilizumab; PD-L1 inhibitors BMS-936559, TECENTRIQ® (Atezolizumab), IMFINZI® (Durvalumab), and BAVENCIO® (Avelumab); and CTLA-4 inhibitors YERVOY (ipilimumab) or any other anti-tumor agent disclosed herein).

The disclosed methods can be used to treat any disease where uncontrolled cellular proliferation occurs such as cancers. Thus in one aspect disclosed herein are methods of treating a cancer (such as a melanoma) in a subject comprising administering to the subject fucose. A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer. The methods disclosed herein may also be used for the treatment of precancer conditions such as cervical and anal dysplasias, other dysplasias, severe dysplasias, hyperplasias, atypical hyperplasias, and neoplasias.

The disclosed methods of treatment contemplate the co-administration of an anti-tumor agent. The anti-tumor agent can comprise any anti-tumor agent known in the art including, but not limited to antibodies, tumor infiltrating lymphocytes, checkpoint inhibitors, dendritic cell vaccines, anti-tumor vaccines, immunotherapy, and chemotherapeutic agents. In one aspect, the anti-tumor agent can include, but is not limited to Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), OPDIVO (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Also contemplated herein are chemotherapeutics that are checkpoint inhibitors, such as, for example, PD1/PDL1 blockade inhibitors and/or CTLA4/B7-1 or 2 inhibitors (such as, for example, PD-1 inhibitors lambrolizumab, OPDIVO® (Nivolumab), KEYTRUDA® (pembrolizumab), and pidilizumab; PD-L1 inhibitors BMS-936559, TECENTRIQ® (Atezolizumab), IMFINZI® (Durvalumab), and BAVENCIO® (Avelumab); and CTLA-4 inhibitors YERVOY (ipilimumab).

The combination of fucose and an anti-tumor agent can be formulated in the same composition of separately. Where separate, the fucose can be administered before, after, or concurrently with the anti-tumor agent. Administration of fucose can be accomplished prophylactically or therapeutically.

The disclosed methods of treating and enhancing immune responses comprising the administration of fucose, have the functional effect of being an adjuvant. It is understood and herein contemplated that the disclosed methods of treating and/or enhancing immune responses can comprise the administration of any known fucose including L-fucose, D-fucose, or any other known fucose isomer including phosphorylated fucose including, but not limited to fucose-1-phosphate (a.k.a., phosphorylated L-fucose), and/or GDP-L-fucose.

Lectin-Mediated Proximity Ligation (L-PLA)

Currently, no antibodies specifically recognize fucosylated species of specific proteins. Click chemistry methods allow for global metabolic labeling of all fucosylated (or otherwise glycosylated) proteins in live cells using alkyne- or azide-conjugated sugars. Click chemistry reactions allow one to "click" in a label of choice (either a fluorophore or a tag such as biotin conjugated to either alkyne or azide). However, the limitation of that method is that (i) probed material must be live, and (ii) one cannot visualize the sugar-modified species of a specific protein.

Figure 8:
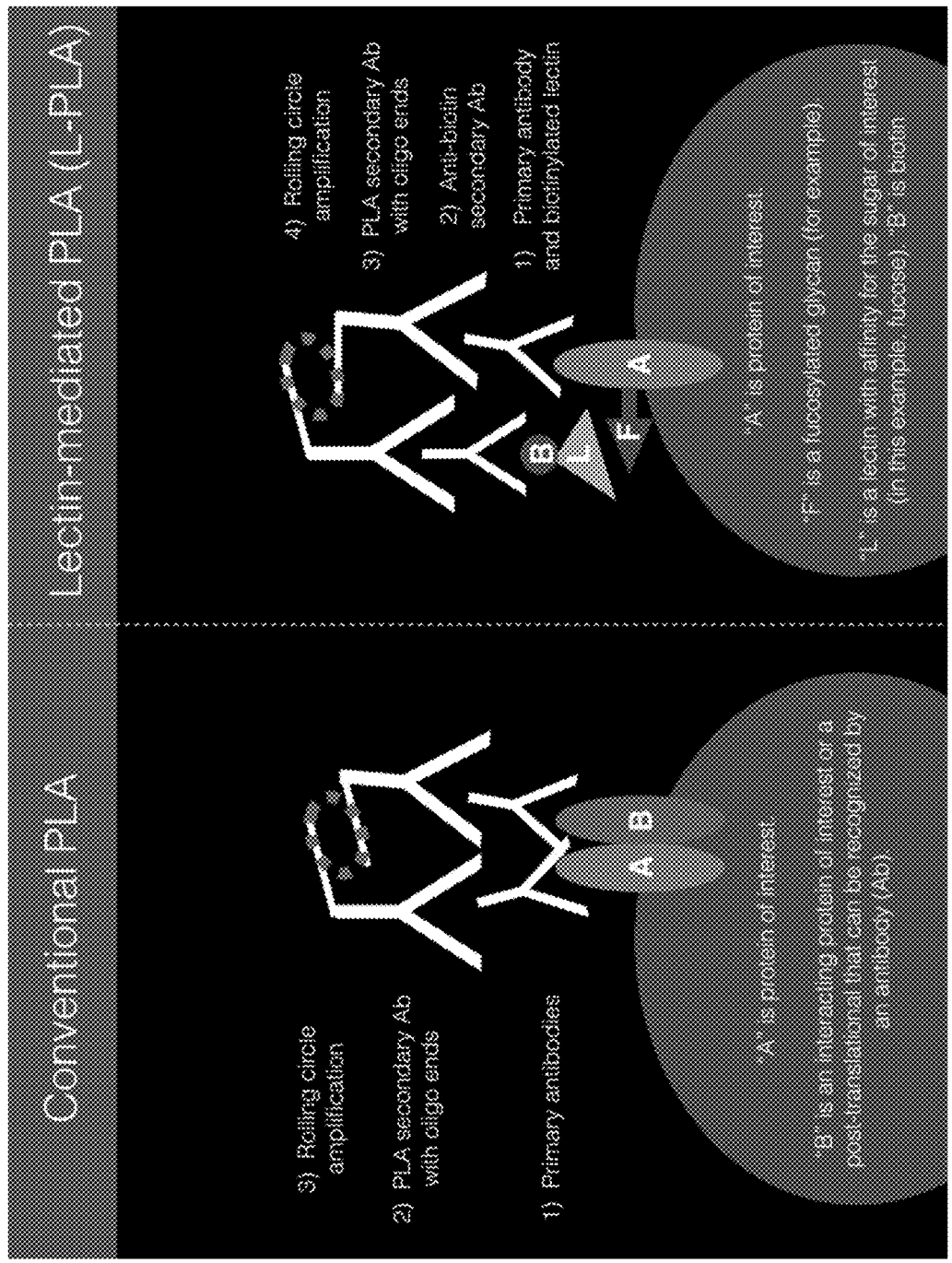
FIG. 8 shows a schematic of how lectin-mediated proximity ligation works.

In order to circumvent this problem and visualize fucosylated specified of specific individual proteins, the proximity ligation (PLA) technique was modified from a 2-layer sandwich detection method to a 3-layer detection method using biotinylated lectin. The "conventional" proximity ligation is a method that allows for the detection of either 2 interacting proteins or a post-translationally modified (e.g., phosphorylated) species of antibody. The caveat of this method is that it requires 2 different primary antibodies that can either recognize the 2 different interacting proteins or the target protein and the post-translational modification on the target protein. By contrast, the lectin-mediated proximity ligation (L-PLA) allows the ability to visualize sugar-modified species of a specific protein. In brief (see FIG. 8), the cells (seeded on coverslips, fixed) or tissues (mounted on slides, deparaffinized and subjected to standard antigen retrieval) are incubated with a primary antibody against the protein of interest and a biotinylated lectin that recognizes the sugar of interest (for example, for fucose, biotinylated Ulex europaeus agglutinin 1 (UEA1) or *Aleuria aurantia* lectin (AAL) lectins were used, which have different affinities for different fucose linkages on fucosylated proteins. For other glycosylation modifications with other sugars, one only needs to switch to other lectins with specificities for the sugar of interest). After incubation, the cells/tissue are washed, then incubated with anti-biotin secondary antibody, and then washed and incubated with PLA secondary antibodies that can bind to the anti-biotin secondary and the primary antibody against the protein of interest. Lastly, PLA ligation and rolling circle amplification are performed. This technique works successfully in cells, and it represents a highly sensitive method for detecting fucosylated/glycosylated species of proteins in fixed patient tissue samples for enhanced diagnostic/prognostic assessment/biomarkers for cancer and other pathologies.

Thus, in one aspect, disclosed herein are methods of detecting a sugar modified protein comprising contacting the protein of interest with a first antibody that specifically binds to the protein of interest and a lectin (including a labeled lectin, such as a biotinylated lectin) that recognizes the sugar of interest, contacting the lectin with a second antibody that specifically binds to the lectin or a label on the lectin, contacting the first antibody that bound the protein of interest with a third antibody that specifically binds the first antibody and contacting the second antibody with a fourth antibody that recognizes the second antibody; wherein the third and fourth antibodies are conjugated to complementary oligonucleotides; annealing the oligonucleotides, and amplifying the annealed oligonucleotides by a rolling circle amplification polymerase chain reaction (PCR). It is understood and herein contemplated that as the presence of sugar modified proteins on the surface of a cell is coextensive with checkpoint inhibitors, the disclosed methods to detect a sugar modified protein can also be used to detect the presence of a checkpoint inhibitor on a cancer cell or cancerous tissue.

It is understood and herein contemplated that the disclosed method will work with any glycosylated protein regardless of the sugar or type of glycosylation (for example N-linked, O-linked, C-linked, and Phospho-Serine glycosylation). For example, in one aspect disclosed herein are methods of detecting a sugar modified protein wherein the sugar comprises a glucose (for example N-acetyl-glucosamine), a galactose (for example, N-acetyl-galactosamine), mannose, fucose, xylose, or N-acetylneuraminic acid. Thus, in one aspect, disclosed herein are methods of detecting a sugar modified protein wherein the sugar of the sugar modified protein is fucose.

To successfully detect the sugar of the modified protein, the disclosed method employs labelled lectins that specifically recognize the sugar moiety. For example, when the modifying sugar is fucose, the lectin can be a labeled UEA1 or AAL lectin. Example of lectins for use in the disclosed methods include, but are not limited to fucose binding lectins UEA and AAL (as well as AAA and AOL), N-acetylneuraminic acid binding lectins Elderberry lectin (SNA), *Maackia amurensis* leucoagglutinin (MAL), and *Maackia amurensis* hemoagglutinin (MAH), N-acetyl-glucosamine binding lectin wheat germ Agglutinin (WGA), N-acetyl-galactosamine binding lectins ricin (RCA), peanut agglutinin (PNA), jacalin (AIL), and hairy vetch lectin (VVL), and mannose binding lectins concanavalin A (ConA), lentil lectin (LCH), and snowdrop lectin (GNA).

In one aspect, the disclosed methods of detecting sugar-modified proteins further employs the use of a label such as, for example, biotin, or other exogenous, non-mammalian label (e.g., FLAG, MYC, V5, GST, HA, which can be conjugated to the lectin and detected by a secondary antibody. Such labels are optional, but provide a ready target for a secondary antibody (such as the second antibody of the method). In one aspect, the lectin can be conjugated to or modified with a label prior to binding the protein.

Also disclosed herein are L-PLA methods wherein the third and fourth antibodies are recognize the same antigen.

As noted herein, the presence of a sugar modified protein (such as, for example HLA-DRB1) on the surface of a cell (such as, for example a cancer cell) is coextensive with the presence of a check point inhibitor on the surface of the cell. Accordingly, in one aspect, disclosed herein are methods of detecting the presence of checkpoint inhibitors in a cancer comprising detecting a sugar modified protein (such as, for example HLA-DRB1) comprising obtaining a cancerous tissue sample from a subject, subjecting the tissue sample to lectin-mediated proximity ligation (L-PLA) for fucosylated HLA-DRB1, lectin (such as, for example, *Aleuria aurantia* lectin (AAL)) pulldown, or flow cytometry with an anti-lectin or antibody specific for the sugar modified protein; wherein the presence of a sugar modified protein on the cancer cell indicates the presence of a checkpoint inhibitor on the surface of a cancer cell.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Definitions

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "bispecific antibody" refers to an antibody having two different antigen-binding regions defined by different antibody sequences. This can be understood as different target binding but includes as well binding to different epitopes in one target.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "protein" (if single-chain), "polypeptide" and "peptide" are used interchangeably herein when referring to a gene product, e.g., as may be encoded by a coding sequence. When referring to "polypeptide" herein, a person of skill in the art will recognize that a protein can be used instead, unless the context clearly indicates otherwise. A "protein" may also refer to an association of one or more polypeptides. By "gene product" is meant a molecule that is produced as a result of transcription of a gene. Gene products include RNA molecules transcribed from a gene, as well as proteins translated from such transcripts.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e g immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1: Fucosylation and Immune Surveillance

Figures 1A, 1B, 1C:
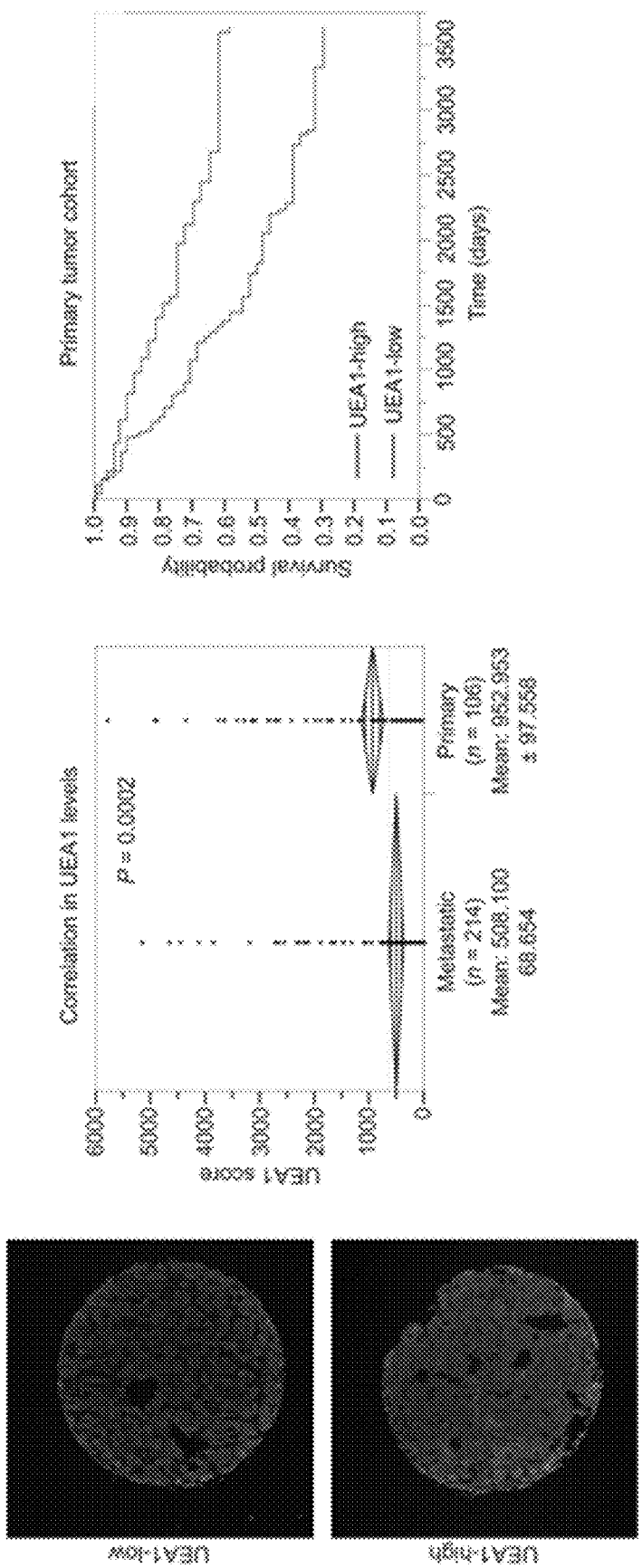

100. Fucosylation has an important role in immune suppression of melanoma tumors. To determine whether cellular fucosylation correlates with melanoma progression, a melanoma tumor tissue microarray containing over 300 patient tumor biopsies was immunostained using UEA1, a lectin that binds to fucosylated proteins (green), and HMB45/S100 cocktail, specific markers for melanoma cells (red). UEA1 signals were measured within HMB45/S100-positive melanoma cells and correlated UEA1 intensity with melanoma progression. A ~50% reduction in fucosylation in metastatic compared with primary lesions was observed. To determine whether fucosylation levels correlate with survival outcome, primary tumor specimens were dichotomized according to high vs. low UEA1 signals and analyzed their correlation with survival probability (FIG. 1).

Figure 2A:
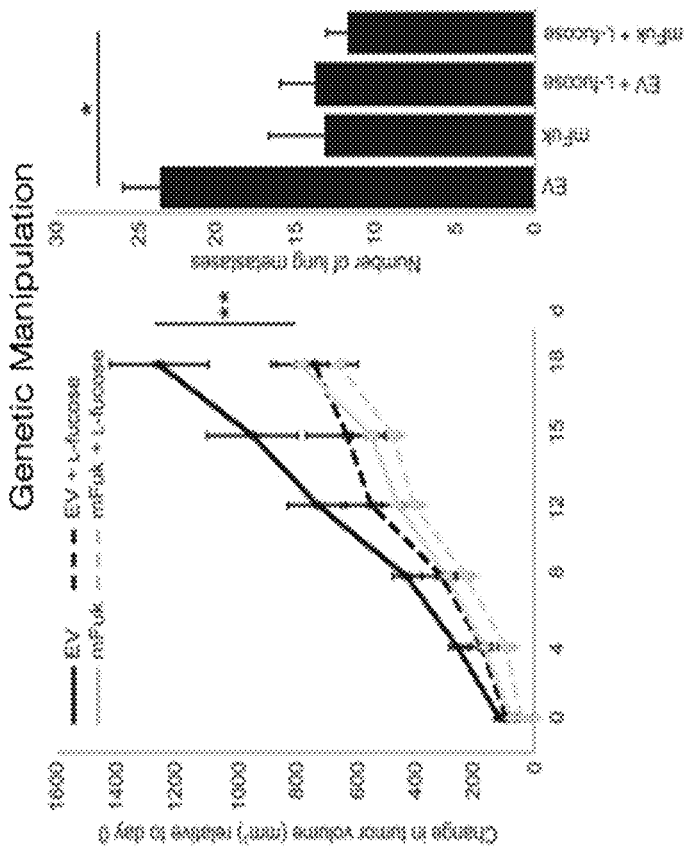
Figure 2B:
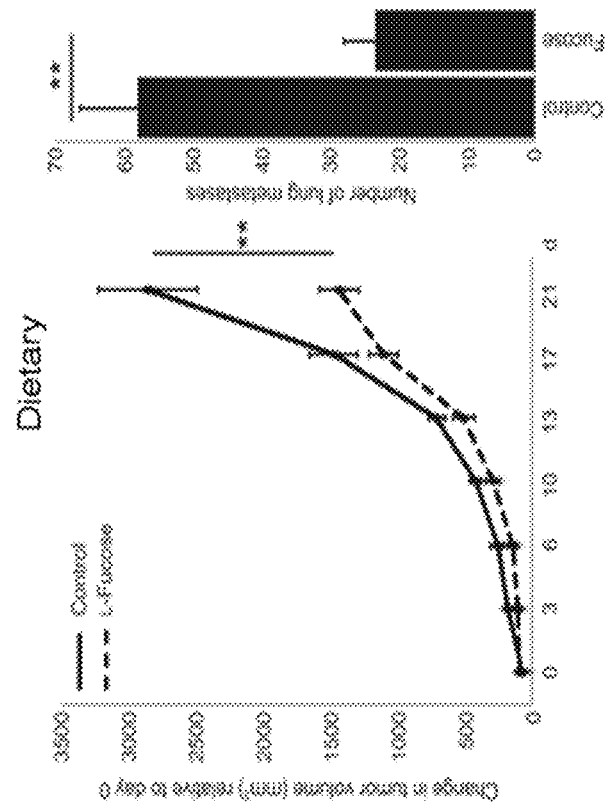
Figure 2C:
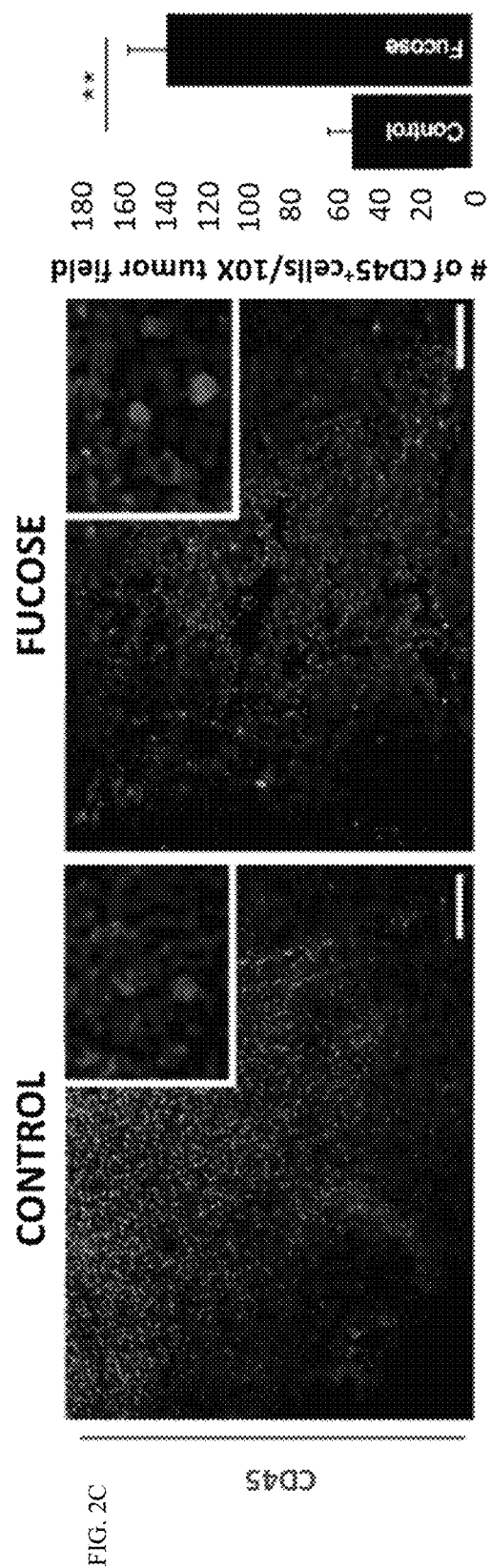
Figure 2D:
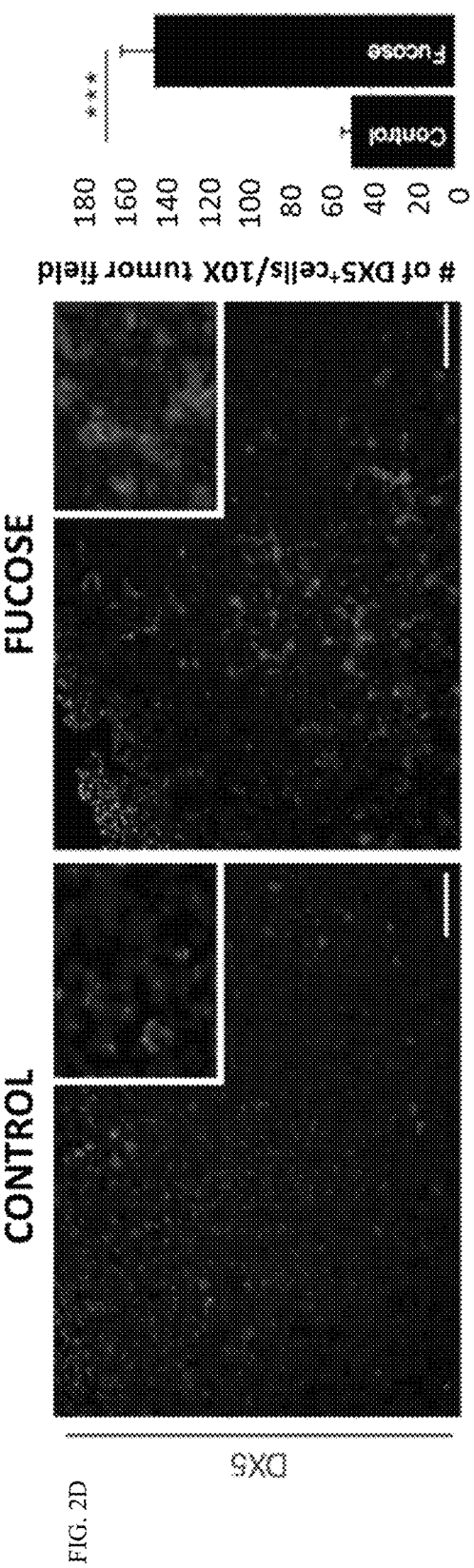

To determine whether dietary or genetic modulation of fucosylation affects tumor growth and metastasis, we previously studied a mouse melanoma model in which tumor fucosylation was increased either by dietary supplementation (FIG. 2A) with 100 mM fucose or by overexpressing mouse FUK (FIG. 2B). Increasing fucose irrespective of route resulted in increased tumor suppression. To determine whether fucosylation affects tumor infiltration by immune cells, Immunofluorescent staining analysis of CD45 (general leukocyte marker, red) and DAPI (blue) was performed (FIG. 2C). To determine whether fucosylation affects tumor infiltration by NK cells, immunofluorescent staining analysis for DX5 (an NK cell marker, red) and DAPI (blue) was performed (FIG. 2D). Both NK cells and CD4+ T cells were elevated in samples from fucose supplemented mice.

Figure 3B:
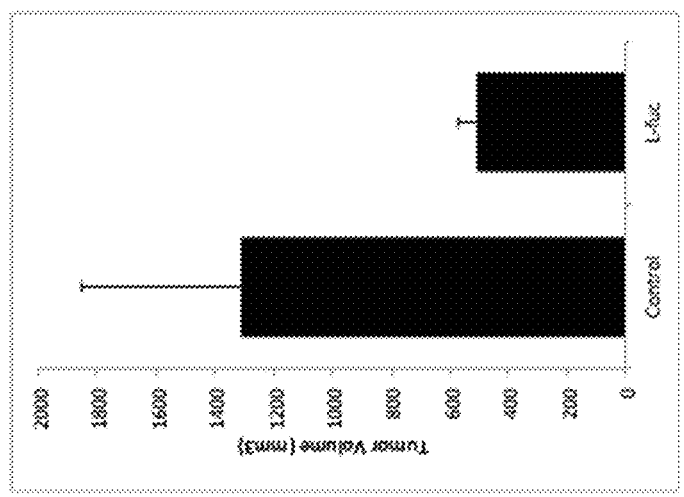
Figure 3A:
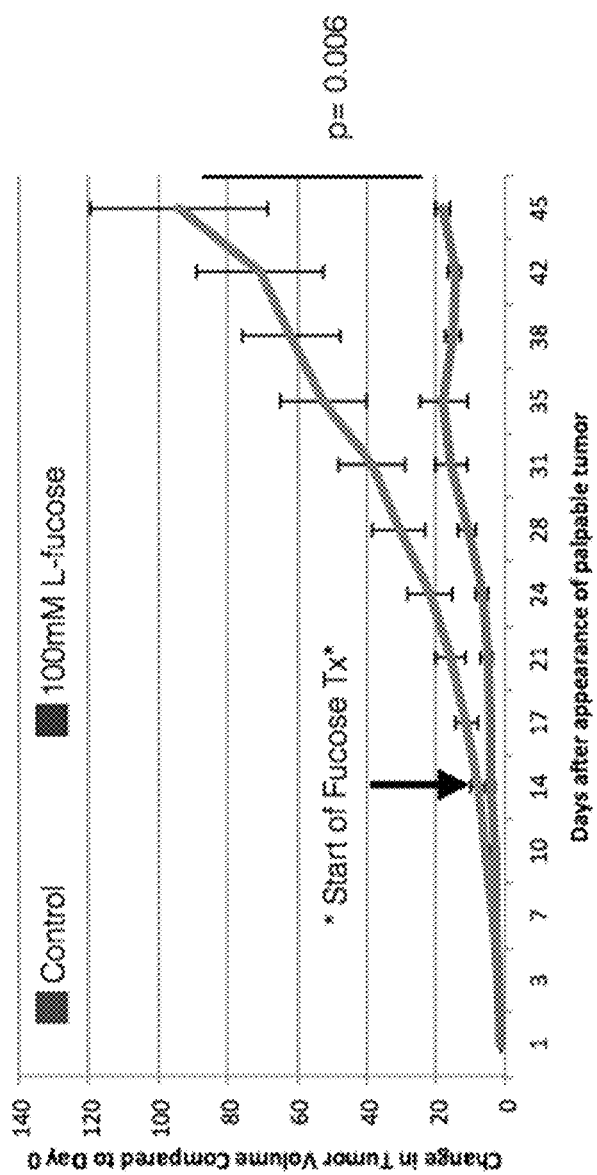
Figure 3D:
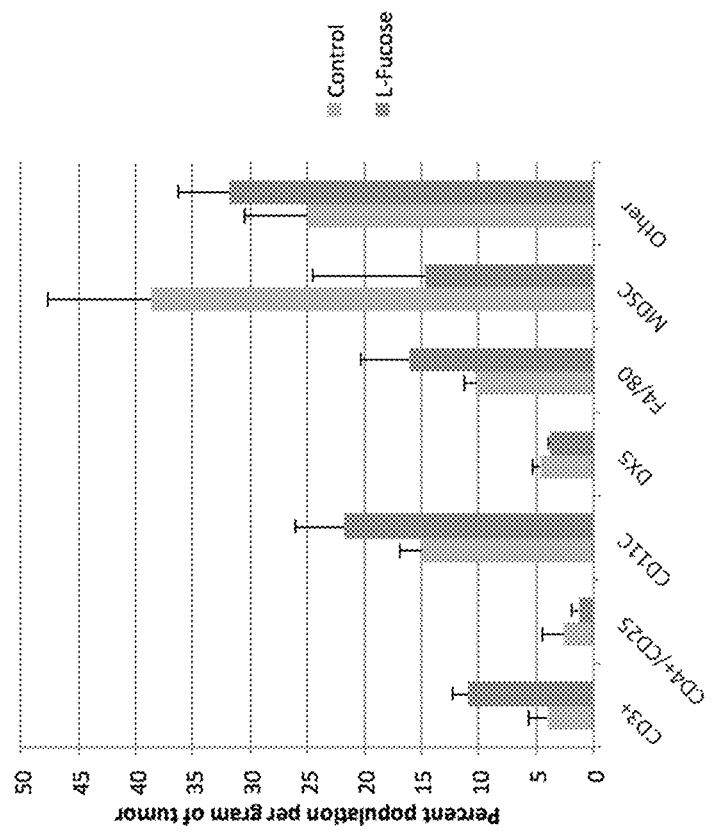
Figure 3C:
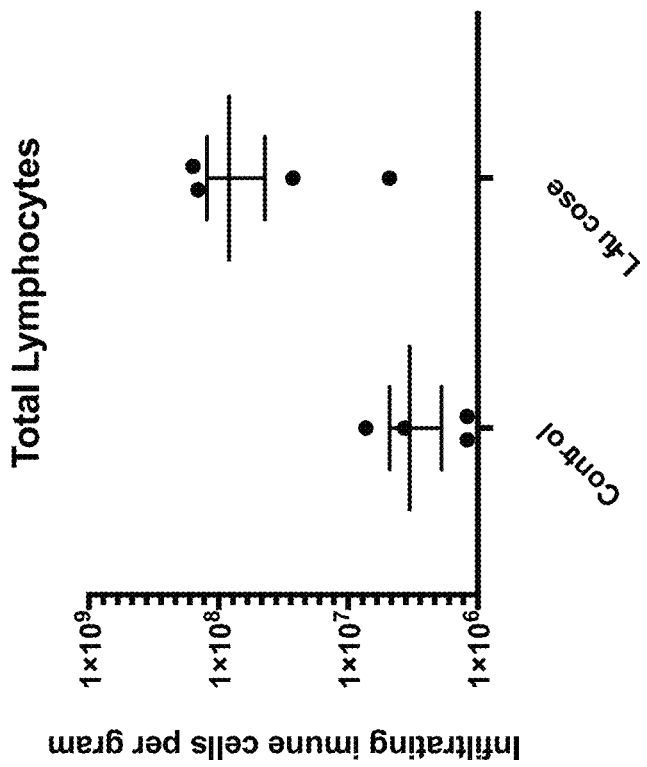

To determine which immune cell populations were affected by L-fucose, another mouse melanoma model treated with control or L-fucose-supplemented water was used. First, $1.25 \times 10^6$ SW1 mouse melanoma cells were injected into the back right flanks of the mice and allowed the tumors to grow to 150 mm³. At 150 mm³ (14 days), 100 mM L-fucose was administered via the drinking water to half of the mice. Tumor growth was monitored (FIGS. 3A and 3B). Total and specific subpopulations of tumor-infiltrating lymphocytes were assessed by cell flow cytometric analysis (FIGS. 3C and 3D). Assessed populations included F4/80 (macrophage)-, Gr-1 (MDSCs)-, Cd11c (Dendritic cells)-, and DX5 (NK cells)-positive cells. For T-cells, we probed for CD3 (general T-cell marker) and further for CD4 and CD8 (for those T cell subpopulations). Of the CD4-positive cells, CD25 positive cells was used to elucidate the T regulatory cells. The data show that overall immune infiltration of tumors is increased in response to dietary fucose supplementation. Both CD4 and CD8 positive T cells (CD3+ cells) increased in response to fucose. However, myeloid derived suppressor cells (MDSCs) decreased in response to dietary fucose supplementation.

Increasing fucosylation suppresses melanoma tumors, it was observed that the >50% reduction in tumor growth triggered by L-fucose supplementation is associated with significant increases in infiltration of tumors by CD45+ immune cells and natural killer (NK) cells. This SW1 melanoma tumor/C3H mouse isogenic model was recapitulated to profile—in detail—tumor-infiltrating immune populations. >65% reduced tumor growth was observed during dietary L-fucose supplementation (FIG. 4A). Flow cytometric analyses revealed that the tumors from L-fucose-supplemented mice contain 10-50-fold more infiltrating immune cells (per gram of tumor) than tumors from mice on control diet, indicating that fucosylation enhances immune suppression of tumors. Although most tumor-suppressive immune cell types were increased in the fucosylation-high, smaller tumors, tumor-infiltrating CD4+ and CD8+ T cells were most increased-doubled-in these tumors compared to control diet tumors (FIG. 4B, left and right). To determine whether CD4+ or CD8+ T cells are required for L-fucose-triggered melanoma tumor suppression, the melanoma mouse model above was repeated but added cohorts of mice in which either CD4+ or CD8+ T cells were immunodepleted. The immunodepletion models revealed that loss of CD4+ T cells significantly, but not CD8+ T cells, abrogated tumor suppression (FIG. 4C, left and right) and reduced numbers of intratumoral CD8+ T cells, CD11c+ dendritic cells (DCs), and NK cells (FIG. 4D), indicating that during L-fucose treatment, CD4+ T cells are required for intratumoral recruitment of these cell types to suppress tumor growth. The presence and cytolytic activity of CD4+ T cells in tumors has been correlated with better patient survival rates and increased responsiveness to immunotherapies, respectively.

The possibility that tumor fucosylation can directly activate the tumor cell-killing activity of NK cells was explored. To assay for this possibility, a lactate dehydrogenase (LDH)-release-based assay was used in which the fucosylation of LU1205 melanoma cells was modulated prior to co-culture with NK cells. Specifically, primary NK cells isolates (5A) or immortalized NK92 cell line (5B) were co-cultured with 1205Lu melanoma cells that were pre-treated with DMSO, 250 µM pan-fucosyltransferase inhibitor (FUTi), or 250 µM L-fucose for 8 hours. Non-radioactive LDH-release cytotoxicity assay was performed to measure extent of NK cell-mediated killing. The findings show that increasing tumor fucosylation alone is sufficient to induce the tumor-cell killing activity of both immortalized and primary human NK cells (FIGS. 5A and 5B) Immunoblot analysis using AAL lectin (another fucose-binding lectin) was performed to confirm the effects of FUTi (5C) or L-fucose (5D) on 1205Lu cells (96 h treatment). (•: p-value≥0.02) (*: p-value≥0.002).

Figure 6:
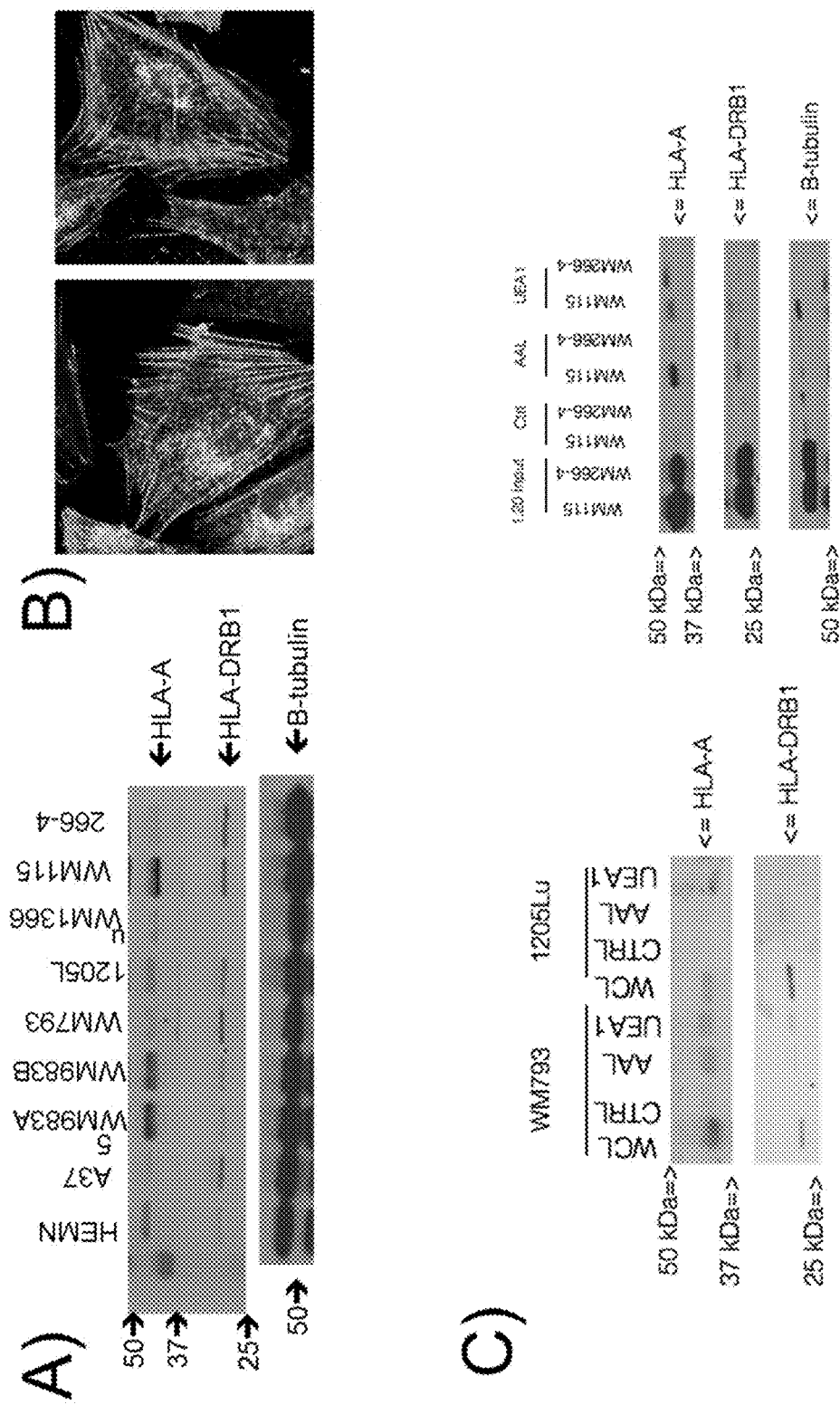
Figure 7:
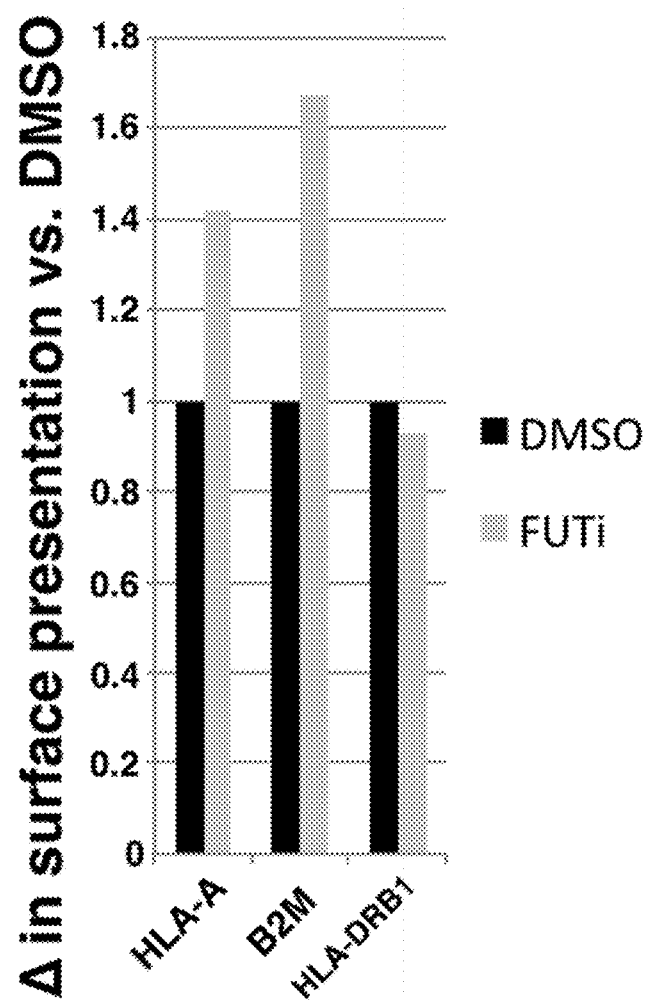

To determine molecular mechanisms underlying the effects of fucosylation, a click-chemistry-based proteomic screen was performed to identify all fucosylated proteins in melanoma cells. 2 fucosylated immunomodulatory proteins, HLA-A and HLA-DRB1, were identified in melanoma cells. Fucose-binding lectin pulldown and immunoblot analysis confirmed the i) the expression and ii) the fucosylation of these 2 HLA proteins in melanoma cells, and further, indicate that their fucosylation is reduced when comparing patient-matched primary vs. metastatic cell lines (FIGS. 6A & 6C). The proximity ligation analysis technique, a cutting edge technique conventionally implemented to visualize 2 directly interacting proteins or post-translationally modified species of specific proteins when antibodies for the modifications are available (e.g., phosphorylated Tyr using an anti-phospho-Tyr antibody). However, as there are no antibodies specific for fucosylated moeities, biotinylated AAL lectin and HLA-A- or HLA-DRB1-targeted antibodies were used to adapt generally double-layer PLA protocols into a triple-layer PLA protocol (a.k.a., lectin-mediated PLA, or L-PLA) to visualize fucosylated HLA-A and HLA-DRB1. The results reveal that fucosylated HLA-A and HLA-DRB1 localize to punctae throughout the cell (FIG. 6B). To further characterize the effects of fucosylation on HLA-A and HLA-DRB1, preliminary flow cytometric assessment of the cell surface presentation of these 2 proteins was performed. The results indicate that inhibiting global fucosylation results in the increased surface presentation of HLA-A and its binding partner, β2-microglobulin, whereas modulation of fucosylation did not appear to alter the surface presentation of HLA-DRB1 (FIG. 7). These data indicate that fucosylation suppresses the surface presentation of HLA-A.

Together, the data indicates roles for fucosylation and HLA-A/HLA-DRB1 in promoting immune cell-mediated melanoma cell killing. Reduced fucosylation, as is observed during melanoma progression, impairs immune surveillance of melanoma tumors. However, the observations highlight the potential implementation of dietary L-fucose supplementation as a non-toxic, effective therapeutic agent to boost immune-mediated suppression of melanoma tumors. L-fucose (pre-) supplementation can enhance the efficacy of current immunotherapeutic approaches (e.g., Nivolumab or TIL therapy), particularly in patients who do not exhibit upfront responsiveness. The studies herein elucidate: (a) how fucosylation regulates HLA-A/HLA-DRB1 and the interaction between melanoma and CD4+ T cells (and other immune cells), and (b), whether fucosylation/fucosylated HLA-A/HLA-DRB1 correlates with responsiveness (clinical parameters) of melanomas to current immunotherapies (e.g., Nivolumab or TIL therapy). The studies disclosed herein highlight how fucosylation/fucosylated HLA-A/HLA-DRB1 can be exploited as a novel adjuvant for therapeutic modalities and enhanced patient stratification, improving patient response rates and durations of response to immunotherapy.

a) Determination of how L-Fucose and Melanoma Tumor Fucosylation Affect CD4+ T Cell Biology and CD4+ T Cell-Dependent Tumor Suppression:

(1) Verify Altered CD4+ T Cell-Regulated TILs in Systemic L-Fucose Treatment vs. Tumor-Specific Fucosylation CD4+ T cells are required for L-fucose-mediated melanoma tumor suppression (FIGS. 4B & 4C). However, the relative contribution of systemic fucosylation vs. tumor cell fucosylation (or both) to the tumor suppression observed are unclear. Mouse FUK was ectopically overexpressed in melanoma cells to increase tumor fucosylation and similar tumor suppression as dietary (systemic) L-fucose supplementation was observed. However, the precise contribution of tumor cell-specific fucosylation to the CD4+ T cell-mediated recruitment of other immune cell types and tumor suppression remains to be delineated. To address these issues, the model in FIGS. 4A and 4C can be repeated using SW1 mouse melanoma cells expressing either empty vector (control) or mouse Fuk (mFuk; to genetically increase fucosylation). Briefly, control empty vector (EV)- or mFuk-overexpressing SW1 murine melanoma cells can be injected into the rear flanks of C3H/HeJ mice. The mice can also be immunodepleted (or not) of CD4+ T cells as previously described. Mouse cohort number calculations are described in Data and Statistical Analysis Plan section. Upon reaching 1.5 cm$^2$, the tumors were harvested, and immune cells can be isolated and profiled by flow cytometry. Profiling markers included F4/80, CD11b, CD163, CD206 (macrophages and polarization); GR-1 (MDSCs); CD11c (DCs); CD14 (monocytes); CD3, CD4, CD8, CD25, FoxP3, CD69, 41BB, PD1, Tim-3, BTLA, and Lag-3 (T cells and activation, and Tregs), CD19 (B cells), and NKp46 (NK cells) (see FIG. 3D). This experiment addresses the question of systemic vs. tumor-specific fucosylation contribution, as well as CD4+ T cell-mediated alterations to tumor-infiltrating immune cell landscape.

(2) Determine Signaling Changes in CD4+ T Cells Induced by Tumor Fucosylation and Systemic L-Fucose To determine how fucose/fucosylation is affecting crucial signaling pathways in CD4+ T cells, phosphoproteomic analyses can be performed on CD4+ T cells isolated from either control or mFUK-expressing SW1 tumors or from SW1 tumors from mice treated±dietary L-fucose as detailed above. The CD4+ T cells can be immediately harvested from the models above in parallel to flow studies above using standard antibody-magnetic bead-based isolation methods and subject to phosphoproteomic analyses, followed by Ingenuity Pathway Analysis. These analyses allow for unbiased global profiling to identify significant signaling changes induced in CD4+ T cells by both systemic fucose and melanoma tumor-specific fucosylation. CD4+ T cell signaling pathways found to be significantly altered by tumor fucosylation can be verified by IB and qRT-PCR analyses using the mouse CD4+ T cells harvested, as well as human CD4+ T cells.

(3) Investigate the Contribution of Dendritic Cells (DC) to CD4+ T Cell-Mediated Melanoma Suppression Given the observation of the L-fucose-triggered, CD4+ T cell-dependent increase in DC and NK cells, it is possible that CD4+ T cells are first stimulated by tumor fucosylation (i.e., fucosylated HLA) to recruit DCs, which facilitate antigen processing/presentation to recruit other immune subtypes including NK cells. To test the possibility that DC cells are crucial downstream effectors of CD4+ T cells in this context.

Control- or mFUK-expressing SW1 tumor or SW1 tumor±L-fucose supplementation models were conducted as above as detailed above, in which the mice can be subject to CD4+ T cell depletion (or not). In addition, the mice can be injected with (or not) an agonistic CD40 antibody that has been used in previous studies to activate DC cells. This approach can be used to activate DC cells independently of CD4+ T cell presence. The mice can be monitored for tumor growth, and effects on TILs can be assessed by flow as detailed above. Mouse cohort number calculations are described in Data and Statistical Analysis Plan section.

(4) Verification with Patient-Matched TIL-Derived CD4+ T and Tumor Cells

In order to validate the findings relating the effects of fucosylation on CD4+ T cells, patient-matched T and tumor cells can be used. CD4+ T cells can be sorted from the patient T cells by magnetic bead method. Either the melanoma cells alone ("tumor autonomous fucosylation") or both the melanoma and CD4+ T cells ("systemic L-fucose treatment") can be pre-treated with DMSO (control), 250 µM FUTi, or 250 µM L-fucose to modulate fucosylation. The melanoma cells can then be co-cultured with the CD4+ T cells over a time course of 8 h. Every 2 h, co-culture CD4+T cells can be harvested and assessed for activation analysis by ELISA for γ-IFN, as well as for markers of the signaling pathway(s) identified to be activated. Further, there are currently limited numbers (<30) of de-identified patient tumor digests that have been cryopreserved. In vitro co-culture cytotoxicity assays (as in FIG. 5) can be performed using the patient-matched tumor cell lines for those digests. The patient tumor cell lines can be pretreated with DMSO (control) 250 µM FUTi, or 250 µM L-fucose to modulate fucosylation, followed by co-culture using the TIL-containing patient-matched TILs. The requirement for CD4+ T cells can be verified in this in vitro assay by pre-immunodepleting the patient TILs (using magnetic bead method as previously indicated).

The studies disclosed herein delineate the crucial immune effects induced by systemic L-fucose vs. tumor cell-specific fucosylation. Further, these studies elucidate how fucosylation triggers CD4+ T cell activation (signaling changes) and infiltration into melanoma tumors by systemic fucose and tumor-specific fucosylation. The studies also delineate requirement/role of DCs downstream of CD4+ T cells in this scenario. Where DCs are a predominant and crucial downstream effector of CD4+ T cells, the CD40 agonistic antibody can rescue tumor suppression in dietary L-fucose-supplemented, CD4+ T cell immunodepleted mice.

b) Determine how Fucosylation of HLA-A/HLA-DRB1 Affects Their Role in Melanoma:Immune Cell Interactions:

(1) Delineate Requirement of HLA-A/HLA-DRB1 in Fucosylation-Stimulated Tumor Suppression and CD4+ T Cell Recruitment, Verify In Vivo Observations In Vitro with De-Identified Patient-Derived TIL First, the requirement for HLA-A/HLA-DRB1 for recruitment/activation of CD4+ T cells was determined by fucosylation. Mouse HLA-A/HLA-DRB1 orthologs (a.k.a., H2K1 and H2EB1) can be knockeddown/overexpressed in SW1 cells that can be isografted into C3H/HeJ mice. Tumor growth can be monitored, and following tumor harvest, infiltrating immune cell populations can be profiled by flow cytometry. FFPE blocks and frozen portions of tumor and spleen can be used to verify the flow analyses (by IF staining and qRT-PCR for markers of immune cells of interest (i.e., CD4+ and CD8+ T cells, DCs, NK cells, etc.).

Next, in vitro co-culture assays can be performed using patient melanoma cell lines that can have knocked down for HLA-A or HLA-DRB1 (using control or targeted shRNAs) and co-cultured±L-fucose with patient-matched CD4+ T cells to assess CD4+ T cell activation. Activation of CD4+ T cells can be verified as described above. Similarly, co-culture cytotoxicity assays (as described in FIG. 5) can be performed using control or CD4+ T cell immunodepleted tumor digests with HLA-A- or HLA-DRB1-knocked down patient tumor-matched cell lines. Loss of either HLA-A or HLA-DRB1 is impairs CD4+ T activation and TIL-mediated cell killing.

(2) Determine how Fucosylation Affects HLA-A/HLA-DRB1 Protein Stability, Subcellular Localization, Partner Binding, and Effects on Immune Cell Activity First, direct fucosylation can be confirmed using the following 2-pronged enzymatic and biochemical approach. HLA-A/HLA-DRB1 immunoprecipitated from control (DMSO) or FUTi-treated human melanoma (WM793 or WM1366) cells can be subjected to enzymatic sugar removal using 3 fucosidases (to remove α1,2; α1,3/4; or α1,2/3/4/6-linked fucose) or PNGaseF (to remove N'-linked glycans, followed by AAL lectin pulldown and immunoblot (IB) analysis for HLA-A/HLA-DRB1, which implicates respective fucose linkages. FUTi can serve as a positive control to block fucosylation, reducing the amount of HLA-A/HLA-DRB1 pulled down by AAL. WM793/WM1366 can be used as they exhibit relatively higher fucosylation than others which allows for more significant chemical modulation of fucosylation. A click-chemistry fucose technique can be used to biotinylate fucosylated exogenously expressed, V5-tagged HLA-A/HLA-DRB1 and detect by V5-IP followed by IB for biotin. Briefly, V5-empty vector- or V5-HLA-A/HLA/DRB1-expressing melanoma cells can be incubated with alkyne-fucose to label all cellular fucosylated proteins. Cells can be lysed and subject to a click reaction using azide-biotin to render fucosylated proteins as biotinylated. Lysates can be subject to V5-IP and IB for biotin (streptavidin) and HLA-A/HLA-DRB1 (simultaneous visualization can be performed using a Li-Cor system). Controls can include non-labeled cells and lysates subject to click reaction without azide-biotin. Visualization of a biotin-positive HLA-A/HLA-DRB1 bands confirms direct fucosylation. For robustness, experiments can be repeated in A375, LU1205, WM115, WM266-4, WM983A/B melanoma lines.

To identify requisite fucosylation sites, V5-tagged exogenously expressed HLA-A and HLA-DRB1 were purified from melanoma cells and subject them to mass spectrometric analysis. In addition, fucosylation site prediction software was used to predict putative fucosylation sites on HLA-A (N110 and T206) and HLA-DRB1 (N48 and T129). Based on these predictions, site (alanine) mutants were generated for each predicted site to abolish potential fucosylation. Upon confirmation of the site(s), these "fucomutants" constructs can be used for reconstitution into melanoma cell lines to evaluate how site-specific fucosylation affects behavior and function of HLA-A/HLA-DRB1.

To assess how fucosylation affects the protein stability of HLA-A/HLA-DRB1, WM793 or WM1366 are treated with DMSO (control), 250 µM FUTi, or 250 µM L-fucose to modulate fucosylation, followed by immunoblot analysis for total levels of HLA-A/HLA-DRB1. This experiment reveals changes in steady-state levels of HLA-A/HLA-DRB1. To further assay changes in HLA-A/HLA-DRB1 protein degradation dynamics, cyclohexamide (CHX) chases can be performed (timecourses where cells are treated with DMSO/FUTi/L-fucose in the presence of CHX, which blocks protein translation/production) or MG132 blocks (where cells are treated with DMSO/FUTi/L-fucose in the presence of MG132, which blocks proteosomal degradation). These experiments can be repeated with exogenous fucomutant HLA-A/HLA-DRB1 constructs to confirm that the exogenous constructs behave the same as the endogenous HLAs. These experiments reveal changes (if any) in the half-life and degradation rates of HLA-A/HLA-DRB1 induced by altered fucosylation.

Figure 4:
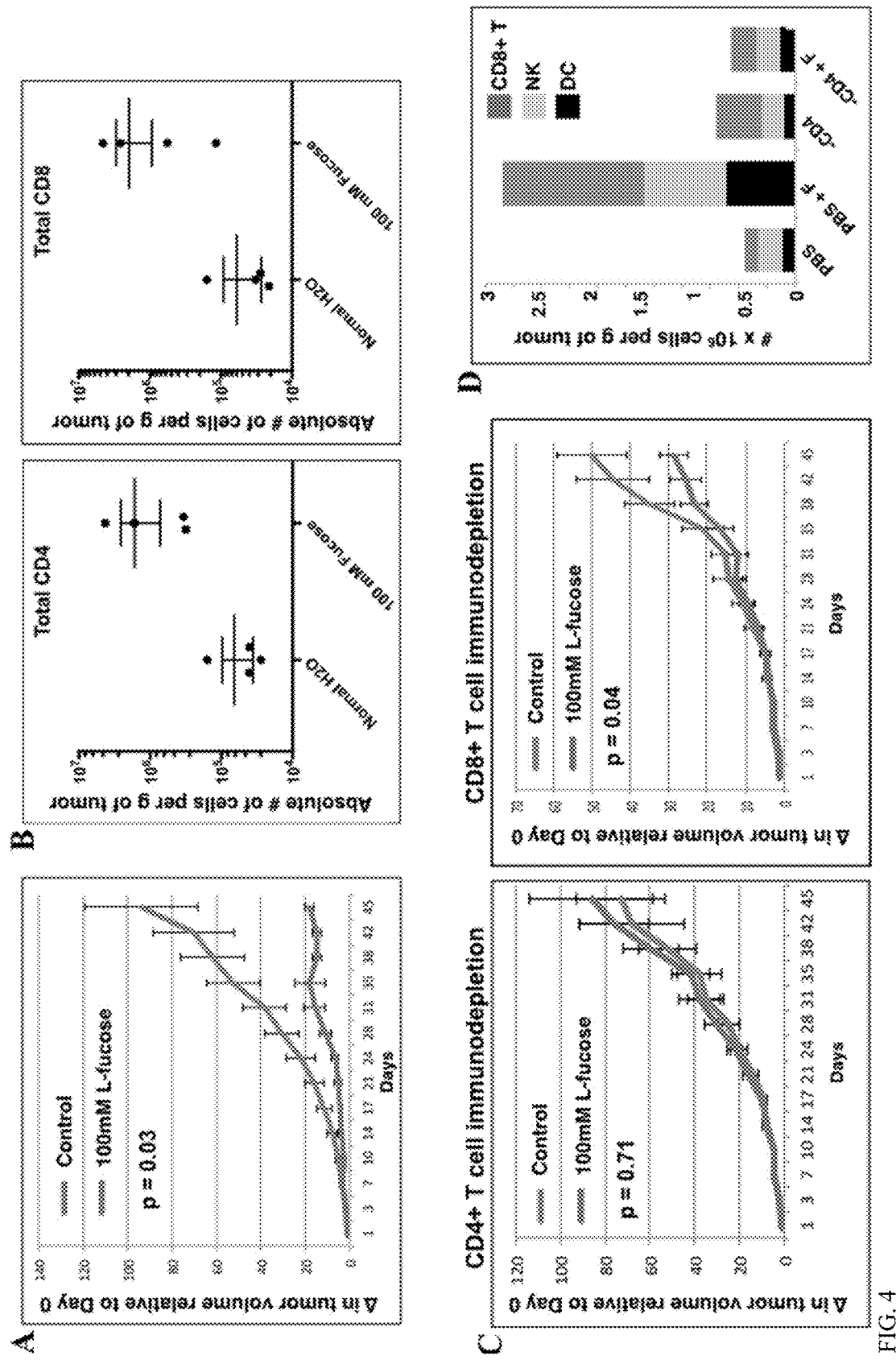

Next, the effects of fucosylation on subcellular localization (and thus function/plasma membrane presentation) of HLA-A/HLA-DRB1 can be tested. Standard immunofluorescence cytochemistry is performed using antibodies against these proteins, as well as L-PLA, on DMSO (control)-, 250 µM FUTi-, or 250 µM L-fucose-treated WM793 and WM1366 cells using lectin- and protein-targeted antibodies followed by immunofluorescent microscopy and ImageJ (NIH) analysis of puncta. Conventional PLA immunofluorescence technique was successfully modified to using fucose-binding AAL lectin (FIG. 4). The results can be further verified on cells treated as detailed above by more in-depth cell surface flow cytometric analyses as described in (FIG. 5). These experiments can be repeated with exogenous fucomutant HLA-A/HLA-DRB1 constructs to confirm that the exogenous constructs behave the same as the endogenous HLAs.

To examine how fucosylation affects partner binding of HLA-A and HLA-DRB1, the V5-tagged WT vs. fucomutant HLA constructs can be expressed, perform V5 IP, followed by IB for known partners. For HLA-A, partners can include β2-microglobulin, and for HLA-DRB1, partners can include HLA-DRA1 or LAGS (to be assessed by in vitro pullday assay using V5-HLA-DRB1 and immune cell lysates).

To verify that the crucial role that site-specific fucosylation plays in CD4+ T activation, de-identified patient-derived melanoma cells can be modified to express wild-type vs. fucomutant HLAs (the patient's HLA-A and HLA-DRB1 can be cloned from their melanoma cell's cDNA). The melanoma cells can be co-cultured with the patient-matched CD4+ T cells over a timecourse of 8 h and assessed for CD4+ T cell activation.

(3) Assess Clinical Correlations Between General Fucosylation and Fucosylated HLA-A/HLA-DRB1 in Nivolumab- or TIL Therapy-Treated Patient Samples.

Lastly, how general melanoma tumor fucosylation vs. fucosylated HLA-A/HLA-DRB1 correlates with clinical parameters (e.g., overall survival or progression-free survival) in Nivolumab or TIL therapy-treated patients can be assessed. This is important for determining whether general tumor fucosylation vs. HLA fucosylation has prognostic utility for immunotherapy in melanoma Immunostaining analysis of the FFPE samples can be performed for AAL/UEA1 lectin and HLA-A/HLA-DRB1 (total and fucosylated (by lectin-PLA, as in FIG. 6B). The tumor sections can be counterstained with MART1, a melanoma marker. Stained tumors are imaged, and lectin/HLA-A/HLA-DRB1/and fucosylated HLA-A/HLA-DRB1 signal intensities are blindly scored from within MART1-positive regions only. The tumor-specific intensities are analyzed for correlation with clinical parameters (e.g., overall survival/time to progression/progression-free survival).

The studies disclosed herein elucidate the role(s) of fucosylation in the regulation of HLA-A/HLA-DRB1. The MS efforts at identifying HLA-A/HLA-DRB1 fucosylation sites allow for the generation of fucomutants for functional studies. The studies shown herein allowed for the determination of whether overall tumor fucosylation, as well as the specific fucosylation of HLA-A and HLA-DRB1, correlate with patient responsiveness to Nivolumab and/or TIL therapy. These findings provide the basis for an efficient patient stratification approach for Nivolumab/TIL therapy using general tumor fucosylation and/or fucosylated HLA-A/HLA-DRB1. L-fucose supplementation mouse model provides support for the concept that L-fucose is an effective and safe adjuvant agent for Nivolumab/TIL therapy. Importantly, the results provide the basis for an adjuvant utility of L-fucose for other immunotherapies in other cancers.

2. Example 2: RPS3 Fucosylation in Melanoma Cell Biology

Melanoma skin cancer is a malignancy that typically arises spontaneously on sun-exposed areas of the skin. Ultraviolet radiation causes DNA damage that over time leads to cellular transformation of melanocytes and initiation of cancer. There is strong selection for mutations in the mitogen activated protein kinase (MAPK) signaling pathway. Indeed, upwards of 75 percent of melanomas are driven by activating mutations in the MAPK kinases NRAS and BRAF in patients affected by this disease. Mutations in this pathway are thought to be an early event in disease development as evidenced by the characterization of NRAS and BRAF mutations in benign nevi, a non-malignant hyperproliferation of melanocytes. This suggests that while MAPK activation is selected for, alterations in other proteins or signaling pathways participate in melanoma progression.

Melanoma cells show a loss of global fucosylation throughout progression, suggesting that posttranslational modification of proteins by the sugar fucose participates in disease advancement. Increasing melanoma fucosylation by genetically altering melanoma cells also slows primary tumor growth and metastatic burden in vivo. Although these findings support a model where loss of fucosylation promotes tumor growth and dissemination, the specific proteins and/or pathways that respond to alterations in fucosylation are not known. Here we provide evidence supporting a role for posttranslational fucosylation of the ribosomal protein S3 (RPS3) in influencing melanoma progression and response to stressors and clinically relevant therapeutic agents.

Figure 9:
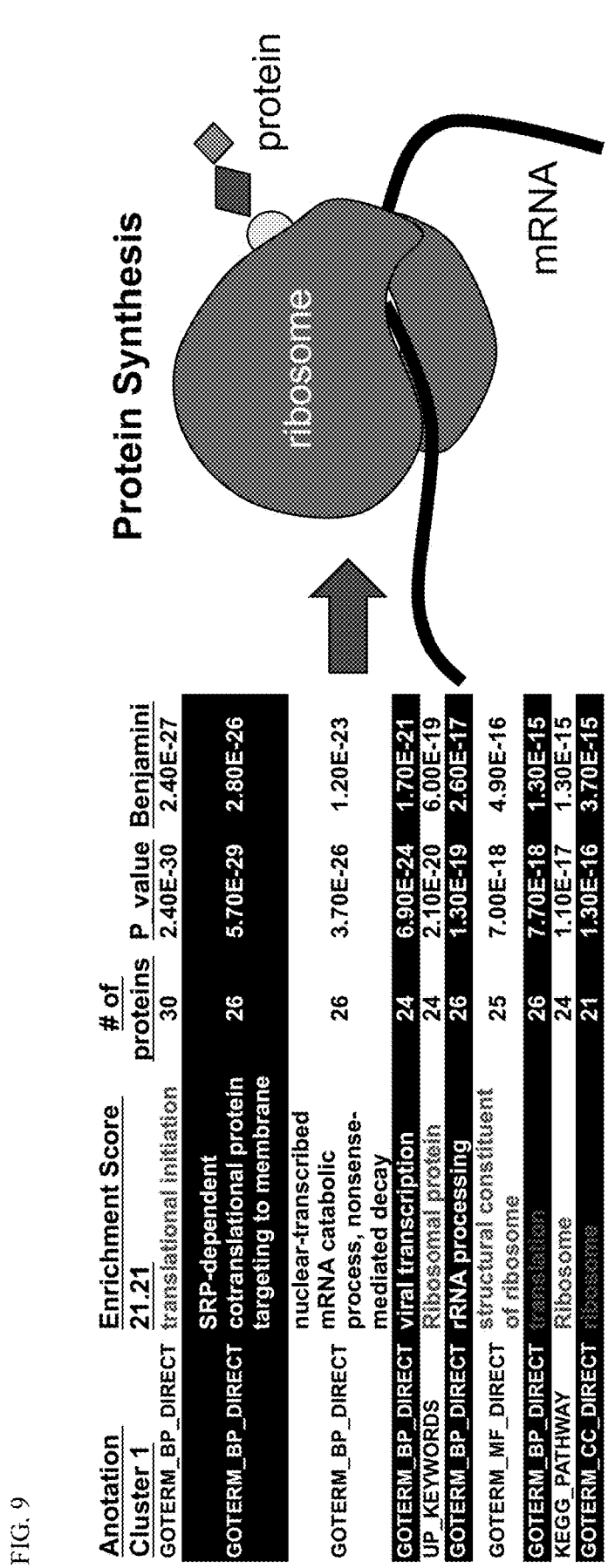
FIG. 9 shows the identities of fucosylated proteins that were isolated from melanoma whole cell lysates by UEAI lectin pull-down (PD) and processed for LC-MS/MS identification.

To identify fucosylated proteins, Fucosylated proteins were isolated from melanoma whole cell lysate by UEAI lectin pull-down (PD) and processed for LC-MS/MS identification (FIG. 9). Proteins with greater than five exclusive unique spectra count (EUSC, ~200 proteins) were analyzed using DAVID functional annotation analysis to identify cellular pathways or processes likely to be influenced by fucosylated proteins. The top annotation cluster showed that proteins involved in ribosome assembly and protein translation are over-represented in the dataset of fucosylated proteins.

Figure 10:
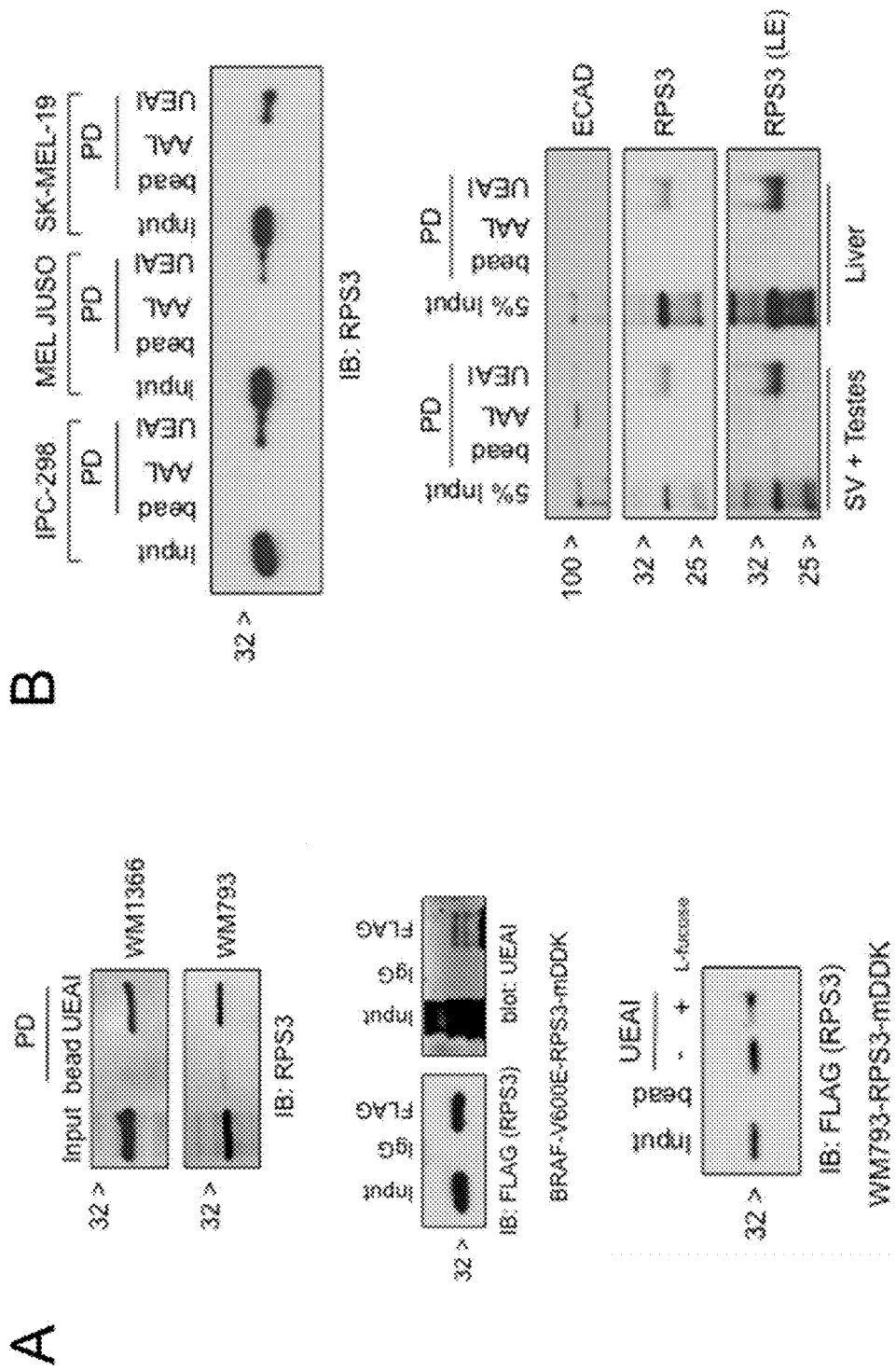
FIGS. 10A and 10B show that the Ribosomal protein S3 is fucosylated (by multiple lectin PD assays using WM793, WM1366, IPC-298, MEL JUSO, SK-MEL-19 melanoma cells, as well as mouse seminal vesicles/testes and liver lysates.
Figure 11A:
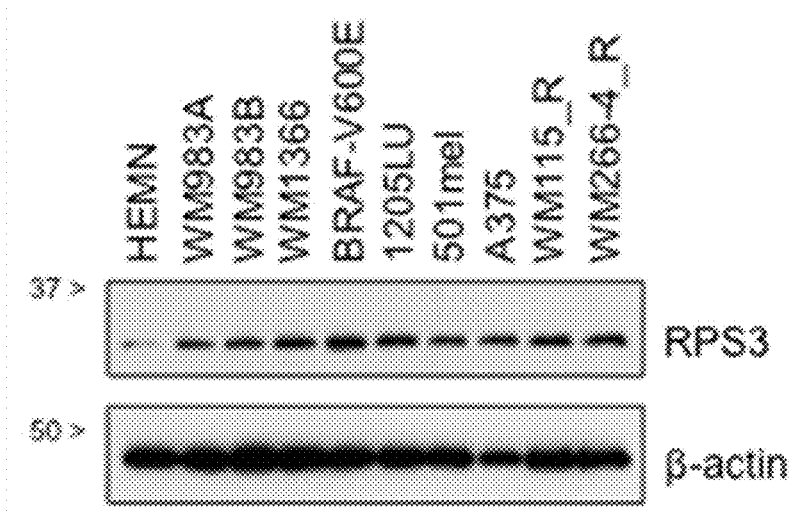
Figure 11B:
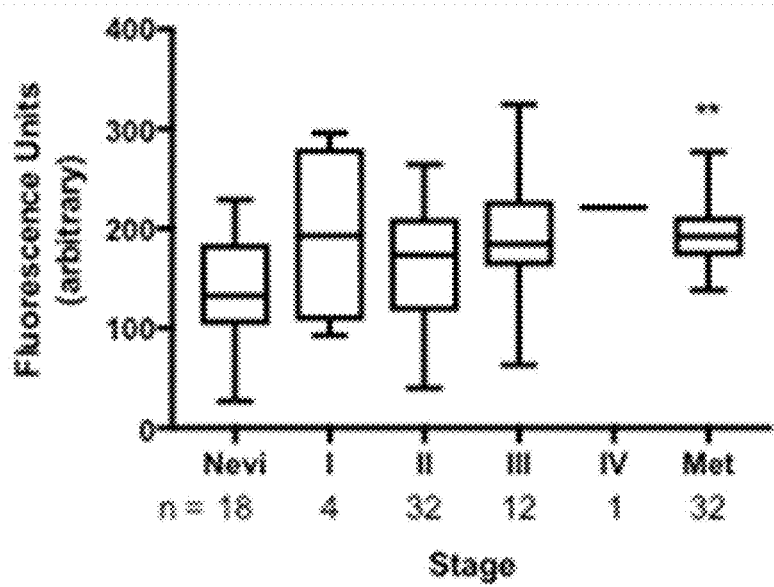
Figure 11C:
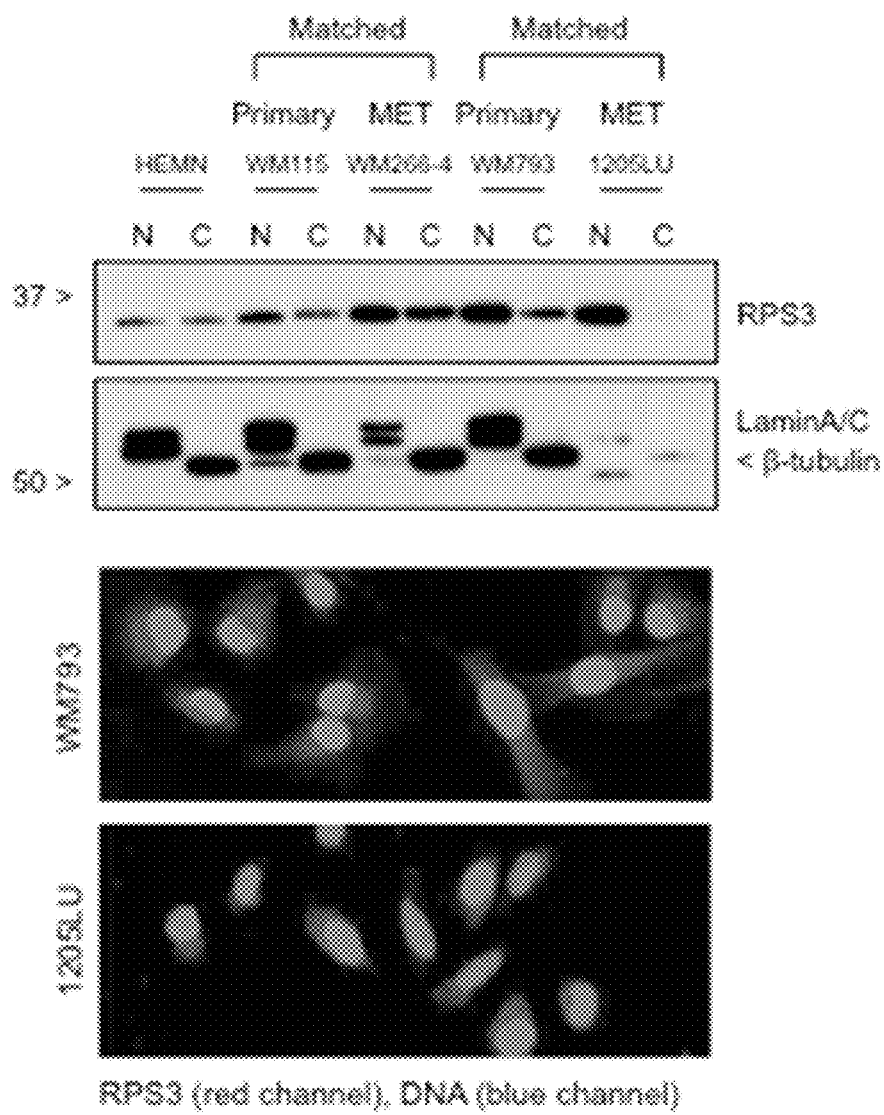

Using a UEAI PD and RPS3 blot, it was shown that RPS3 is recognized by UEAI lectin by IP and lectin blot (FIG. 10A). Exogenous fucose competes for UEAI recognition by PD (FIG. 10B) RPS3 is recognized only by UEAI in cell lines and in vivo.

As shown in FIG. 11, RPS3 is increased in melanoma cells, shows a shift toward nuclear localization throughout progression, and confers an advanced phenotype. Specifically, (11A) RPS3 level in increased in melanoma cells relative to primary melanocytes (HEMN, human epidermal melanocytes). (11B) RPS3 is increased in melanoma through progression in human samples by TMA. TMA stained and analyzed by AQUA at Moffitt Cancer Center Department of Clinical Testing Development Core Facility. (11C) Nuclear RPS3 level increases with stage in matched primary and metastatic (MET) samples relative to HEMN cells (cell fractions analyzed by western blot [left]; cells analyzed by immunofluorescence [right]). (11D) Expression of RPS3-mDDK in vertical growth phase cells confers behavior associated with metastatic disease. Increased anchorage-independent growth [left], increased motility [right]. It was noted that Fucosylated RPS3 level increases in response to cellular stressors. Melanoma cells treated for 24-48 h with serum deprivation (SD), thapsigargin (T, thap) or mutant BRAF-inhibitor (Plexxikon, PLX) and assayed for RPS3 fucosylation by lectin PD (FIG. 12).

It was noted that fucosylated RPS3 is predominantly cytoplasmic by UEAI PD (FIG. 13A). It was further noted by L-PLA that RPS3 is localized in the cytoplasm for RPS3 and UEAI lectin (RPS3-UEAI PLA: red channel, Phalloidin: green channel, Nuclei: blue channel) (FIG. 13B).

To ilucidate proteins that interact with fucosylated RPS3. Proteins were identified by LC-MS/MS (FIG. 14). Protein complexes were immunoprecipitated from WM793-RPS3-mDDK lysate by FLAG IP. Complexes were eluted with FLAG peptide and subsequently subjected to UEAI PD to purify protein complexes containing fucosylated RPS3.

3. Example 3: Fucosylated DRB1: a Biomarker for Checkpoint Inhibitors

HLA-DRB1 is expressed (FIG. 15A) and fucosylated (FIG. 15B) in melanoma cells. shRNA knockdown of the mouse ortholog of HLA-DRB1 (IEβ in this mouse model) abrogates L-fucose-triggered tumor suppression vs. control shRNA (SCR) in the SW1 mouse melanoma:syngeneic C3H/HeJ mouse model (FIG. 15C), indicating that HLA-DRB1 is required for L-fucose-triggered tumor suppression. Fucosylation of HLA-DRB1 occurs on amino acid N48 (mutation to G abolishes interaction with fucose-binding AAL lectin) (FIG. 16A). Increasing fucosylation (L-fucose treatment) promotes cell surface abundance of HLA-DRB1 (which is expected to increase $CD4^+$ T cell activation) (FIG. 16B). Oral L-fucose suppresses melanoma growth in the SW1/C3H/HeJ model more significantly than anti-CTLA4 or anti-PD1 alone (FIG. 17). L-fucose+anti-PD1 appears to have improved efficacy over anti-PD1 at this timepoint (FIG. 17B; longer timecourse model in progress as of Oct. 11, 2018). Given longer co-treatment, L-fucose+anti-PD1 can exhibit significant tumor suppression. A lectin-mediated proximity ligation technique was developed to visualize fucosylated HLA-DRB1 in cells and tissues (FIG. 18).

What is claimed is:

1. A method of enhancing an immune response in a subject with a tumor, wherein the subject is administered D-fucose, fucose-1-phosphate, or GDP-L-fucose to increase fucosylation and thereby increase the number of tumor infiltrating lymphocytes by at least 10-fold.

2. The method of claim 1, wherein the fucose is administered orally.

3. The method of claim 1, wherein the lymphocytes are NK cells, dendritic cells, or T cells.

4. The method of claim 1, wherein the method further results in at least a 20% reduction in myeloid-derived suppressor cells.

5. A method of treating a cancer in a subject comprising administering to the subject D fucose, fucose-1-phosphate, or GDP-L-fucose and an anti-tumor agent.

6. The method of treating a cancer of claim 5, wherein the anti-tumor agent is an immune checkpoint blockade inhibitor.

7. The method of treating a cancer of claim 6, wherein the immune checkpoint blockade inhibitor is selected from the group consisting of the PD-1 inhibitors lambrolizumab, Nivolumab, pembrolizumab, and/or pidilizumab; the PD-L1 inhibitors BMS-936559, Atezolizumab, Durvalumab, and/or Avelumab; and/or the CTLA-4 inhibitor ipilimumab.

8. The method of treating a cancer claim 5, wherein the fucose is administered orally.

9. The method of treating a cancer of claim 5, wherein the fucose is administered before and/or during administration of the anti-tumor agent.

* * * * *